US010913986B2

(12) United States Patent
Mackenzie et al.

(10) Patent No.: US 10,913,986 B2
(45) Date of Patent: Feb. 9, 2021

(54) METHOD OF IDENTIFYING IMPORTANT METHYLOME FEATURES AND USE THEREOF

(71) Applicant: The Board of Regents of the University of Nebraska, Lincoln, NE (US)

(72) Inventors: Sally A. Mackenzie, Lincoln, NE (US); Robersy Sanchez, Lincoln, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 530 days.

(21) Appl. No.: 15/422,409

(22) Filed: Feb. 1, 2017

(65) Prior Publication Data

US 2017/0218463 A1   Aug. 3, 2017

Related U.S. Application Data

(60) Provisional application No. 62/289,847, filed on Feb. 1, 2016.

(51) Int. Cl.
| | | |
|---|---|---|
| *C12Q 1/6895* | (2018.01) | |
| *G16B 20/00* | (2019.01) | |
| *G16B 30/00* | (2019.01) | |
| *G16B 50/20* | (2019.01) | |
| *G16B 20/20* | (2019.01) | |
| *G16B 40/00* | (2019.01) | |
| *G16H 50/20* | (2018.01) | |

(52) U.S. Cl.
CPC ........... *C12Q 1/6895* (2013.01); *G16B 20/00* (2019.02); *G16B 20/20* (2019.02); *G16B 30/00* (2019.02); *G16H 50/20* (2018.01); *C12Q 2600/13* (2013.01); *C12Q 2600/154* (2013.01); *G16B 40/00* (2019.02); *Y02A 90/10* (2018.01)

(58) Field of Classification Search
CPC ........... C12Q 2600/154; C12Q 1/6827; C12Q 2523/125; C12Q 1/6809; C12Q 1/6895; C12Q 2521/331; C12Q 2600/13; C12Q 2537/164; C12Q 2600/112; C12Q 2600/156; C12Q 1/6883; C12Q 2600/106; C12Q 2537/165; G16B 20/20; G16B 25/00; G16B 40/00; G16B 20/00; G16B 30/00; G01N 2800/50; G01N 2800/52; G01N 33/57484; G01N 2440/12; G01N 2333/91011; G16H 50/20; C12Y 201/01043; C12Y 201/01; C12Y 201/01062; C07K 14/4702; Y02A 40/146; Y02A 90/26; A01H 1/04; A01H 3/00; G06F 19/18; G06F 19/22; G06F 19/24; G06F 19/345; G06F 17/18; A01G 22/00; G06N 7/005; G16C 20/60

See application file for complete search history.

(56) References Cited

U.S. PATENT DOCUMENTS

| | | |
|---|---|---|
| 6,265,171 B1 | 7/2001 | Herman et al. |
| 7,037,650 B2 | 5/2006 | Gonzalgo et al. |
| 7,229,759 B2 | 6/2007 | Olek et al. |
| 7,550,583 B2 | 6/2009 | Xia |
| 7,820,385 B2 | 10/2010 | Rajeevan et al. |
| 7,943,308 B2 | 5/2011 | Lofton-Day et al. |
| 7,972,784 B2 | 7/2011 | Model |
| 8,241,855 B2 | 8/2012 | Berlin |
| 8,273,528 B2 | 9/2012 | Martienssen et al. |
| 8,323,890 B2 | 12/2012 | Laird et al. |
| 8,361,719 B2 | 1/2013 | Jeddeloh et al. |
| 8,394,585 B2 | 3/2013 | Dong et al. |
| 8,399,221 B2 | 3/2013 | Kim et al. |
| 8,399,222 B2 | 3/2013 | Siva et al. |
| 8,404,439 B2 | 3/2013 | Conrad |

(Continued)

FOREIGN PATENT DOCUMENTS

| | | |
|---|---|---|
| CN | 101353703 | 1/2009 |
| WO | 2003/100557 | 12/2003 |

(Continued)

OTHER PUBLICATIONS

Xu Y. et al. Unique DNA methylome profiles in CpG island methylator phenotype colon cancers. Genome Research (2012) vol. 22 p. 283-291.*
Xu et al. Supplemental figures (2012).*
Xu et al. Supplemental Figure Legends (2012).*
Horvath, D. Study of selected phenotype switching strategies in time varying environment. Physics Letters A (2016) vol. 380, p. 1267-1278.*
Horvath (2016) Appendix A1 and A2.*
Feng, S. et al. (2010) Conservation and divergence of methylation patterning in plants and animals. PNAS, vol. 107 No. 19 pp. 8689-8694.*

(Continued)

*Primary Examiner* — Mary K Zeman
(74) *Attorney, Agent, or Firm* — Evan Law Group LLC

(57) ABSTRACT

A computer-implemented method of preparing a set of differentially informative methylated positions (DIMPs) or differentially informative methylated regions (DIMRs) from a sample methylome of an animal or plant having a phenotypic characteristic different from a wild-type of the same species of animal or plant, and the characteristic is associate with differences in methylation of the genome, comprises: providing a computer with the sample methylome, and a reference methylome of the wild-type of the same species of animal or plant; calculating with the computer a divergence between a plurality of cytosine positions of the sample methylome and the reference methylome; and selecting with the computer a set of DIMPs or DIMRs. Each DIMP or DIMR is selected based on an approximation of the energy required to produce the divergence between methylation levels of the plurality of cytosine positions of the sample methylome as compared to the wild-type methylome.

22 Claims, 7 Drawing Sheets

(56) References Cited

U.S. PATENT DOCUMENTS

| | | | |
|---|---|---|---|
| 8,440,404 B2 | 5/2013 | Makarov et al. | |
| 8,586,302 B2 | 11/2013 | Fuhrmann et al. | |
| 8,637,276 B2 | 1/2014 | Kutyavin | |
| 9,914,981 B2 * | 3/2018 | Akpo | A01H 5/00 |
| 2008/0102450 A1 * | 5/2008 | Barrett | C12Q 1/6827 435/6.12 |
| 2008/0261217 A1 | 10/2008 | Melnikov et al. | |
| 2009/0123915 A1 * | 5/2009 | Laird | C12Q 1/6827 435/6.12 |
| 2009/0191548 A1 * | 7/2009 | Berlin | C12Q 1/6881 435/6.12 |
| 2012/0157324 A1 * | 6/2012 | Lizardi | C12Q 1/6886 506/2 |
| 2012/0179389 A1 * | 7/2012 | Reisfeld | G01N 30/8693 702/24 |
| 2012/0251499 A1 * | 10/2012 | Yeom | C12N 15/113 424/93.2 |
| 2012/0284814 A1 | 11/2012 | Mackenzie et al. | |
| 2013/0117877 A1 * | 5/2013 | Akpo | A01H 1/04 800/260 |
| 2014/0157452 A1 | 6/2014 | Mackenzie et al. | |
| 2015/0052630 A1 | 2/2015 | Mackenzie et al. | |
| 2015/0113679 A1 | 4/2015 | Mackenzie et al. | |
| 2015/0189842 A1 | 7/2015 | Mackenzie et al. | |
| 2019/0112659 A1 * | 4/2019 | Carrell | C12Q 1/68 |
| 2020/0109456 A1 * | 4/2020 | Meissner | G01N 33/48 |

FOREIGN PATENT DOCUMENTS

| | | |
|---|---|---|
| WO | 2005/017652 | 2/2005 |
| WO | 2010/086389 | 8/2010 |
| WO | 2015/048665 | 4/2015 |

OTHER PUBLICATIONS

Ma, B. et al. Predicting DNA methylation level across human tissues. Nucleic Acids Research (2014) vol. 42 No. 6 p. 3515-3528.*
Fukuda, K et al. Regional DNA methylation differences between human and chimpanzees are associated with genetic changes, transcriptional divergence and disease genes. Journal of Human Genetics (2013) vol. 58 p. 446-454.*
Fukuda (2013) Supplemental Figures.*
Feng supplemental information (2010).*
Law, J.A. et al., "Establishing, maintaining and modifying DNA methylation patterns in plants and animals", Nature Reviews Genetics, vol. 11, No. 3, pp. 204-220, (2010).
Ramchandani, S. et al., "DNA methylation is a reversible biological signal", Proceedings of the National Academy of Science, vol. 96, pp. 6107-6112, (1999).
Schneider, T.D. "Theory of molecular machines. II. Energy dissipation from molecular machines", Journal of Theoretical Biology, vol. 148, pp. 125-137, (1991).
Bérut, a, et al., "Experimental verification of Landauer's principle linking information and thermodynamics", Nature, vol. 483, pp. 187-190, (2012).
Esteller, M. "Epigenetics in cancer", The New England Journal of Medicine, vol. 358, pp. 1148-1159, (2008).
Shannon, C.E. "A mathematical theory of communication", The Bell System Technical Journal, vol. 27, pp. 379-423,623-656, (1948).
Jaynes, E.T. "Information Theory and Statistical Mechanics", Physical Review, vol. 106, No. 4, pp. 620—630, (1957).
Toyabe, S. et al., "Experimental demonstration of information-to-energy conversion and validation of the generalized Jarzynski equality", Nature Physics, vol. 6, pp. 988-992, (2010).
Xie H. et al., "Genome-wide quantitative assessment of variation in DNA methylation patterns", Nucleic Acids Research, vol. 39, no. 10, pp. 4099-4108, (2011).
Mercadante, D. et al., "Processive pectin methylesterases: the role of electrostatic potential, breathing motions and bond cleavage in the rectification of brownian motions", PLoS One, vol. 9, issue 2, e87581, pp. 1-11, (2014).
Koslover, E.F. et al., "Force fluctuations impact kinetics of biomolecular systems", Physical Review E, vol. 86, pp. 011906-1-011906-9, (2012).
Severin, P.M.D. et al., "Cytosine methylation alters DNA mechanical properties", Nucleic Acids Research, vol. 39, No. 20, pp. 8740-8751, (2011).
Phelps, C. et al., "Single-molecule FRET and linear dichroism studies of DNA breathing and helicase binding at replication fork junctions", Proceedings of the National Academy of Science, vol. 110, No. 43, pp. 17320-17325, (2013).
Rubin, A. et al., "Nonlinear Models of DNA Dynamics", Mathematical Biophysics, chapter 8, pp. 117-138, (2014).
Schmitz, R.J. et al., "Transgenerational epigenetic instability is a source of novel methylation variants", Science, vol. 334, pp. 369-373, (2011).
Havecker, E.R. et al., "Metastable differentially methylated regions within Arabidopsis inbred populations are associated with modified expression of non-coding transcripts", PLoS One, vol. 7, issue 9, e45242, pp. 1-11, (2012).
Armond, J.W. et al., "A stochastic model dissects cell states in biological transition processes", Scientific Reports, vol. 4, No. 3692, pp. 1-9, (2014).
Adami, C. "Information theory in molecular biology", Physics of Life Reviews, vol. 1, pp. 3-22, (2004).
Tribus, M. et al., "Energy and information", Scientific American, vol. 225, No. 3, pp. 179-188, (1971).
Dillenschneider, R, et al., "Memory erasure in small systems", Physical Review Letters, vol. 102, pp. 210601-1-210601-4, (2009).
Liu, Y. et al., "Sequence evolution correlates with structural dynamics", Molecular Biology and Evolution, vol. 29, pp. 2253-2263, (2012).
Schneider, T.D. "Sequence logos, machine/channel capacity, Maxwell's demon, and molecular computers: a review of the theory of molecular machines", Nanotechnology, vol. 5, pp. 1-18, (1994).
Oyeyemi, O.A. et al., "Temperature dependence of protein motions in a thermophilic dihydrofolate reductase and its relationship to catalytic efficiency", Proceedings of the National Academy of Science, vol. 107, pp. 10074-10079, (2010).
Klinman, J.P. et al., "Hydrogen tunneling links protein dynamics to enzyme catalysis", Annual Review of Biochemistry, vol. 82, pp. 471-496, (2013).
Klinman, J.P. "An integrated model for enzyme catalysis emerges from studies of hydrogen tunneling", Chemical Physics Letters, vol. 471, pp. 179-193, (2009).
Schneider, T.D. "70% efficiency of bistate molecular machines explained by information theory, high dimensional geometry and evolutionary convergence", Nucleic Acids Research, vol. 38, No. 18, pp. 59956006, (2010).
Benjamini, Y. "Discovering the false discovery rate", Journal of the Royal Statistical Society Series B Statistical Methodology, vol. 72, pp. 405-416, (2010).
Becker, C. et al., "Spontaneous epigenetic variation in the Arabidopsis thaliana methylome", Nature, vol. 480, pp. 245-249, (2011).
Schmitz, R.J. et al., "Patterns of population epigenomic diversity", Nature, vol. 495, pp. 193-198, (2013).
Dawy. Z. et al., "On genomic coding theory", European Transactions on Telecommunications, vol. 18, pp. 873-879, (2007).
Lorenzo-Ginori, J.V. et al., "Digital signal processing in the analysis of genomic sequences", Current Bioinformatics, vol. 4, pp. 28-40, (2009).
Lawrence, M. et al., "Software for computing and annotating genomic ranges", PLoS Computational Biology, vol. 9, issue 8, e1003118, pp. 1-10, (2013).
Xi, Y. et al., "BSMAP: whole genome bisulfite sequence MAPping program", BMC Bioinformatics, vol. 10, article No. 232, pp. 1-9, (2009).
Lawrence, M. et al., "rtracklayer: an R package for interfacing with genome browsers", Bioinformatics Applications Note, vol. 25, No. 14, pp. 1841-1842, (2009).
Hall, M. et al., "The Weka data mining software: an update", Sigkdd Explorations, vol. 11, issue 1, pp. 10-18, (2009).
Le, S. et al., "FactoMineR: An R package for multivariate analysis", Journal of Statistical Software, vol. 25, issue 1, pp. 1-18, (2008).

(56) References Cited

OTHER PUBLICATIONS

Ma, B., et al. "Predicting Dna methylation level across human tissues", Nucleic Acids Research, vol. 42, no. 6, pp. 3515-3528, (2014).

Bäcklin, C. "Machine learning based analysis of Dna methylation patterns in pediatric acute leukemia", Digital Comprehensive Summaries of Uppsala Dissertations from the Faculty of Medicine 1069, found at uu.diva-portal.org/smash/get/diva2:784373/FULLTEXT01.pdf, pp. 1-70, (2015).

Jombart, T. "adegenet: a R package for the multivariate analysis of genetic markers", Bioinformatics Applications Note, vol. 24, No. 11, pp. 1403-1405, (2008).

Kass, G.V. "An exploratory technique for investigating large quantities of categorical data", Journal of the Royal Statistical Society: Series C, vol. 29, No. 2, pp. 119-127, (1980).

Kumar, S. et al., "Roles, and establishment, maintenance and erasing of the epigenetic cytosine methylation marks in plants", Journal of Genetics, vol. 92, No. 3, pp. 629-666, (2013).

Cortijo, S. et al., "Mapping the epigenetic basis of complex traits", Science, vol. 343, pp. 1145-1148, (2014).

Yang, X. et al., "MutS HOMOLOG1-derived epigenetic breeding potential in tomato", Plant Physiology, vol. 168, No. 1, pp. 222-232, (2015).

Virdi, K.S. et al., "Arabidopsis MSH1 mutation alters the epigenome and produces heritable changes in plant growth", Nature Communications, vol. 6, article No. 6386, pp. 1-9, (2015).

Rabinowicz, P.D. et al., "Genes and transposons are differentially methylated in plants, but not in mammals", Genome Research, vol. 13, pp. 2658-2664, (2003).

Li, X. et al., "High-resolution mapping of epigenetic modification of the rice genome uncovers interplay between DNA methylation histone methylation, and gene expression", The Plant Cell, vol. 20, pp. 259276, (2008).

Frommer, M. et al., "A genomic sequencing protocol that yields a positive display of 5-methylcytosine residues in individual DNA strands", Proceedings of the National Academy of Science, vol. 89, No. 5, pp. 1827-1831, (1992).

Tost, J. et al., "Analysis and quantification of multiple methylation variable positions in CpG islands by pyrosequencing™", BioTechniques, vol. 35, No. 1, pp. 152-156, (2003).

Herman, J.G. et al., "Methylation-specific PCR: A novel PCR assay for methylation status of CpG islands", Proceedings of the National Academy of Science, vol. 93, No. 18, pp. 9821-9826, (1996).

Wang, X. et al., "Genome-wide and organ-specific landscapes of epigenetic modifications and their relationships to mRNA and small RNA transcriptomes in maize", The Plant Cell, vol. 21, pp. 1053-1069, (2009).

Wojdacz, T.K. et al., "Methylation-sensitive high resolution melting (MS-HRM): A new approach for sensitive and high-throughput assessment of methylation", Nucleic Acids Research, vol. 35, No. 6, e41, pp. 1-7, (2007).

Umezu, T. et al., "Detection method for quantifying global DNA methylation by fluorescence correlation spectroscopy", Analytical Biochemistry, vol. 415, No. 2, pp. 145-150, (2011).

Flusberg, B.A. et al., "Direct detection of DNA methylation during single-molecule, real-time sequencing", Nature Methods, vol. 7, No. 6, pp. 461-465, (2010).

Gonzalgo, M.L. et al., "Rapid quantitation of methylation differences at specific sites using methylation-sensitive single nucleotide primer extension (Ms-SNuPE)", Nucleic Acids Research, vol. 25, No. 12, pp. 2529-2531, (1997).

Chinnusamy, V. et al., "RNA-directed DNA methylation and demethylation in plants", Science in China Series C: Life Sciences, vol. 52, No. 4, pp. 331-343, (2009).

Franco-Zorrilla, J.M. et al., "Dna-binding specificities of plant transcription factors and their potential to define target genes", Proceeding of the National Academy of Science, vol. 111, No. 6, pp. 2367-2372, (2014).

Wei, L. et al., "Dicer-like 3 produces transposable element-associated 24-nt siRNAs that control agricultural traits in rice", Proceedings of the National Academy of Science, vol. 111, No. 10, pp. 3877-3882, (2014).

Zhai, J. et al., "Rapid construction of parallel analysis of RNA end (PARE) libraries for illumina sequencing", Methods, vol. 67, pp. 84-90, (2014).

Rosas-Cárdenas, F.D.F. et al., "A simple and efficient method for isolating small RNAs from different plant species", Plant Methods, vol. 7, pp. 1-7, (2011).

Vidal, E.A. et al., "Integrated RNA-seq and sRNA-seq analysis identifies novel nitrate-responsive genes in *Arabidopsis thaliana* roots", BMC Genomics, vol. 14, pp. 1-15, (2013).

Eldem, V. et al., "Genome-wide identification of miRNAs responsive to drought in peach (*prunus persica*) by high-throughput deep sequencing", PLoS One, vol. 7, No. 12, e50298, pp. 1-14, (2012).

Barber, W.T. et al., "Repeat associated small RNAs vary among parents and following hybridization in maize", Proceedings of the National Academy of Science, vol. 109, no. 26, pp. 10444-10449, (2012).

Gommans, W.M. et al., "Sample preparation for small Rna massive parallel sequencing", Methods in Molecular Biology, vol. 786, pp. 167-178, (2012).

Stacy, E.W. "A Generalization of the Gamma Distribution", The Annals of Mathematical Statistics, vol. 33, pp. 1187-1192, (1962).

Crooks, G.E. "The Amoroso Distribution", arXiv:1005.3274v2, pp. 1-27, (2015).

Lienhard, J.H. et al., "A physical basis for the generalized gamma distribution", Quarterly of Applied Mathematics, vol. 25, No. 3, pp. 330-334, (1967).

Khodabin, M. et al., "Some properties of generalized gamma distribution", Mathematical Sciences, vol. 4, No. 1, pp. 9-28, (2010).

Suksaengrakcharoen, S. et al., "A new family of generalized gamma distribution and its application", Journal of Mathematics and Statistics, vol. 10, No. 2, pp. 211-220, (2014).

Akaiki, H. "A new look at the statistical model identification", IEEE Transactions on Automatic Control, ac-19, No. 6, pp. 716-723, (1974).

Schwarz, G. "Estimating the dimension of a model", The Annals of Statistics, vol. 6, No. 2, pp. 461-464, (1978).

Geistlinger, L. et al., "From sets to graphs: towards a realistic enrichment analysis of transcriptomic systems", Bioinformatics, vol. 27, pp. i366-i373, (2011).

Geistlinger, L. et al., "Bioconductor's EnrichmentBrowser: seamless navigation through combined results of set- & network-based enrichment analysis", BMC Bioinformatics, vol. 17, No. 45. pp. 1-11, (2016).

Sanchez, R. et al., "Information thermodynamics of cytosine DNA methylation", PLoS One, vol. 11, issue 3, pp. 1-20, (2016).

Sanchez, R. et al., "Genome-wide discriminatory information patterns of cytosine DNA methylation", International Journal of Molecular sciences, vol. 17, No. 6, pp. 1-26, (2016).

Wiley, R.H. "Signal detection and animal communication", Advances in the Study of Behavior, vol. 36, pp. 217-247, (2006).

Wiley R.H. "Signal detection, noise, and the evolution of communication", Animal Communication and Noise, Animal Signals and Communication 2, Chapter 2, pp. 7-30, (2013).

Wiley, R.H. "A receiver-signaler equilibrium in the evolution of communication in noise", Behaviour, vol. 150, pp. 957-993, (2013).

Definition of "Probability density function" printed from Wikipedia, the free enyclopedia on Aug. 6, 2020 found at https://en.wikipedia.org/wiki/Probability_density_function.

Definition of "Weibull distribution" printed from Wikipedia, the free enyclopedia on Aug. 6, 2020 found at https://en.wikipedia.org/wiki/Weibull_distribution.

Definition of "CpG site" printed from Wikipedia, the free encyclopedia on Sep. 8, 2015 found at https://en.wikipedia.org/wiki/CpG_site.

Definition of "Epigenetics" printed from Wikipedia, the free encyclopedia on Aug. 24, 2015 found at https://en.wikipedia.org/wiki/Epigenetics.

(56) References Cited

OTHER PUBLICATIONS

Definition of "Metaheuristic" printed from Wikipedia, the free encyclopedia on Aug. 24, 2015 found at https://en.wikipedia.org/wiki/Metaheuristic.
Definition of "List of Mathematical symbols" printed from Wikipedia, the free encyclopedia on Oct. 10, 2015 found at https://en.wikipedia.org/wiki/List_of_mathematical_symbols.
Wang, X. et al., "SeqGSEA: A bioconductor package for gene set enrichment analysis of RNA-seq data integrating differential expression and splicing", Bioinformatics, vol. 30, pp. 1777-1779, (2014).
Kuan, P.F. et al., "statistical framework for illumine DNA methylation arrays", Bioinformatics, vol. 26, No. 22, pp. 2849-2855, (2010).
Ali, I. et al., "An identification and prediction methods for feature-subsets of CpG islands methylation based on human peripheral blood leukocytes of chromosome 21q", $33^{rd}$ Annual International Conference of the IEEE Engineering in Medicin and Biology Society, pp. 3233-3236, (2011).
de la Rosa Santamaria, R. et al., "MSH1-induced non-genetic variation provides a source of phenotypic diversity in sorghum bicolor", PLoS One, vol. 9, issue 10, pp. 1-8, (2014).
Robinson, M.D. et al., "Statistical methods for detecting differentially methylated loci and regions", Frontiers in Genetics, vol. 5, article 324, pp. 1-7, (2014).
International Search Report and Written Opinion dated May 30, 2017 for PCT application No. PCT/US2017/016101, 20 pages.
Meyer, D. et al., "Misc functions of the department of statistics, probability theory group (formerly: E1071), TU Wien", pp. 1-62, (2015).

\* cited by examiner

METHOD OF IDENTIFYING IMPORTANT METHYLOME FEATURES AND USE THEREOF

BACKGROUND

Cytosine DNA methylation (CDM) is one of the molecular processes that comprise and effect epigenetic modifications to the genome, and is a widespread regulatory factor in living organisms. Cytosine methylation arises from the addition of a methyl group to a cytosine's C5 carbon residue to form 5-methylcytosine. The biochemical reaction is catalyzed by methyltransferases recruited into complex multicomponent molecular machines [1]. The reverse process of methyl group removal is catalyzed by demethylases [2]. These epigenetic modifications can regulate the transcriptional activity of the corresponding genes or maintain genome integrity by repressing transposable elements and influencing long-term gene silencing mechanisms [1, 5]. Plants and animals respond to environmental changes, and epigenetic factors (as well as genetic factors) are involved in a phenotypic range of this response. Changes introduced by DNA methylation can be inherited from one generation to the next.

Plant genomes contain relatively large amounts of 5-methylcytosine [45]. Other than silencing transposable elements and repeated sequences, the biological roles of 5-methylcytosine are still emerging. Intercrossing a low methylation mutant plant with a normally methylated plant resulted in heritable changes in DNA methylation in the plant genome that affected some plant phenotypic traits [46].

Intentionally creating or breeding for DNA methylation changes or new combinations of DNA methylation patterns in the genome that are useful in agriculture is an emerging technology area that is still in commercial development. One epigenetic modification system that has the potential to improve yields in crop plants is the Msh1 system. Suppression of Msh1 in plants or plant cells giving rise to plants, that when subsequently outcrossed and/or self-pollinated to restore Msh1 function, have been found to produce increase yields and useful traits in the progeny through several methods [47]. These traits are heritable, non-genetic changes in plant phenotypes, depending on the crossing schemes used [48]. These plants contain new DNA methylation patterns [49].

Animal genomes also contain 5-methylcytosine. Variations in the methylome of animals can also be associated with different traits. For example cancer and asthma, and a complex disorder like obesity, are associated with spontaneous abnormal epigenetic reprogramming.

Cytosine can be deaminated by a variety of chemical, thermal, or enzymatic steps to produce uracil and ammonia, while 5-methylcytosine is more resistant to deamination. A common method of converting cytosine, but not 5-methylcytosine, to uracil is to treat DNA with bisulfite. After bisulfite treatment, non-methylated cytosines are converted to uracil while 5-methylcytosine is not converted. Bisulfite treatment provides a convenient chemical treatment method to determine which cytosines are methylated or unmethylated in the methylome by measuring the amount of cytosine to uracil conversion in a bisulfite treated sequences in comparison to an untreated control.

In natural environments, cells from the same tissue are not necessarily in the same state and, consequently, the corresponding cytosine sites may not be at the same methylation status. The methylation status of particular cytosine sites is often expressed in terms of methylation level $p_i = \#C_i/(\#C_i + \#nonC_i)$, where $\#C_i$ and $\#nonC_i$ represent the numbers of methylated and non-methylated read counts observed at the genomic coordinate i, respectively.

Methods for computationally analyzing the DNA methylation data are available although none have proven very useful for correlating the status of the DNA methylome with the phenotypes of the plant or animal being analyzed. The current state of the art in DNA methylome analysis makes use of differentially methylated positions (DMPs), which are single genomic positions for which a significant statistical difference between the methylation levels from two different samples or two groups of samples is detected by the application of a suitable statistical test. Typically, one sample is wild-type (a reference lacking a phenotypic characteristic of interest), and the other sample has a phenotypic characteristic of interest. Several statistical tests have been proposed to assess the detection of DMPs, some of which are the Fisher exact test, binomial test, logistic regression and beta binomial regression. A similar approach can be used for methylation over a region of the genome to calculate differentially methylated regions (DMRs). Correlating phenotypic characteristics affected by methylation of a plant or animal, with the patterns of DMPs and DMRs in the DNA methylome of the plant or animal, has proved difficult.

SUMMARY

In a first aspect, the present invention is a computer-implemented method of preparing a set of differentially informative methylated positions (DIMPs) or differentially informative methylated regions (DIMRs) from a sample methylome of an animal or plant having a phenotypic characteristic different from a wild-type of the same species of animal or plant, and the characteristic is associate with differences in methylation of the genome, comprising: providing a computer with the sample methylome, and a reference methylome of the wild-type of the same species of animal or plant; calculating with the computer a divergence between a plurality of cytosine positions of the sample methylome and the reference methylome; and selecting with the computer a set of DIMPs or DIMRs. Each DIMP or DIMR is selected based on an approximation of the energy required to produce the divergence between methylation levels of the plurality of cytosine positions of the sample methylome as compared to the wild-type methylome.

In a second aspect, the present invention is a method of preparing a collection of sets of DIMPs or DIMRs from a plurality of sample methylomes each prepared from one of a plurality of animals or plants, each animal or plant being of the same species and each animal or plant having the same or similar phenotypic characteristic different from wild-type of the same species, comprising preparing a set of DIMPs or DIMRs for each sample methylome, using a single reference methylome, wherein each set of DIMPs or DIMRs is prepared by the previous methods.

In a third aspect, the present invention is a method of selecting positions and/or regions of differential methylation indicative of a phenotypic characteristic from a plurality of sample methylomes of different animals or plants of a single species, at least one having the phenotypic characteristic different from a wild-type of the same species, comprising providing a computer with the sample methylomes, a reference methylome of the wild-type of the same species, and a collection of DIMPs or DIMRs prepared by the previous methods; and selecting positions and/or regions of differential methylation indicative of the phenotypic characteristic.

In a fourth aspect, the present invention is a method of preparing a set of plants harboring a characteristic associate with differences in methylation of the genome, comprising preparing epigenetic variants of a wild-type plant; breeding the plant, to prepare progeny plants; examining the methylome of progeny plants for the presence of positions and/or regions of differential methylation indicative of the characteristic; and preparing the set of plants by selecting those plants having the positions and/or regions of differential methylation indicative of the characteristic in their methylome. The positions and/or regions of differential methylation indicative of the characteristic are prepared by the previous methods.

In a fifth aspect, the present invention is a method of selecting one or more plants harboring a characteristic associated with differences in methylation of the genome, comprising examining the methylome of plants for the presence of positions and/or regions of differential methylation indicative of the characteristic; and selecting one or more plants having the positions and/or regions of differential methylation indicative of the characteristic in their methylome. The positions and/or regions of differential methylation indicative of the characteristic are prepared by the previous methods.

In a sixth aspect, the present invention is a method of selecting one or more seeds or plants harboring a useful agronomic trait from a set of one or more candidate plants comprising comparing methylation levels of one or more diagnostic DIGRs or DIMRs previously associated with a useful agronomic trait in one or more plants to methylation levels of corresponding genomic regions of candidate seeds or plants; and selecting candidate seeds or plants with methylation patterns comprising one or more of said diagnostic DIGRs or DIMRs in one or more of said corresponding genomic regions of candidate seeds or plants.

In a seventh aspect, the present invention is a method of selecting an oligonucleotide useful for identifying seeds or plants harboring a useful agronomic trait comprising providing DIGRs or DIMRs previously associated with a useful agronomic trait in one or more plants; selecting one or more DIMPs within DIGRs or DIMRs for methylation analysis of these genomic regions; and selecting an oligonucleotides that measure DNA methylation levels at said selected DIMPs.

In an eighth aspect, the present invention is an oligonucleotide for detecting DNA methylation changes in a DIGR or a DIMR identified by the previous methods, the oligonucleotide having a nucleotide sequence of the DIGR or the DIMR except at one or more base where there is substitution of an A or I base for a G base, to detected the conversion of an unmethylated C to T due to the chemical treatment.

In a ninth aspect, the present invention is a system for selecting plants with higher yield and/or higher stress tolerance potential, the system comprising a computer or computer network operating a program, and a device for storing data, connect to the computer or computer network, having stored therein data identifying selected DIGRs or DIMRs and characteristic DNA methylation levels associated with DIGRs or DIMRs selected in plants with higher yield and/or higher stress tolerance. The computer program compares DNA methylation levels from said selected DIGRs or DIMRs of candidate seeds of plants to select candidate plants with DNA methylation levels characteristic of one or more DIGR or DIMR methylation patterns associated with higher yield and/or higher stress tolerance.

Definitions

As used herein, the terms "plant" or "plants" refer to a plant in general at all of its propagative stages including seeds, pollen, tissue culture and vegetative propagation.

As used herein, the term "methylome" refers to the methylation status of the DNA sequences being analyzed whether these sequences comprise all of the genome, part of the genome, or a selected subset of the genome.

As used herein, the terms "isogenic" or "variety" refer to plants with the essentially the same genome sequence, allowing for minor DNA sequence differences consistent with DNA replication errors that at natural error rates that do not typically create new phenotypes. Isogenic plants or plants of the same variety can have different appearances and/or phenotypes due to significant DNA methylation differences such as introduced by Msh1-suppression, expression or inhibition of DNA methyltransferases, or breeding of the methylome to alter its methylation levels.

As used herein, the phrase "higher yield and/or higher stress tolerance potential" refers to the ability of the current plant to give rise to progeny that display higher yield and/or higher stress tolerance whether the progeny are produced by self-pollination or outcrossed or both of the current plant.

As used herein, the phrases "epigenetic" or "epigenetic modifications" or "epigenetic modification" refer to heritable and reversible epigenetic changes that include methylation of chromosomal DNA, and in particular methylation of cytosine residues to 5-methylcytosine residues. Changes in DNA methylation of a region are often associated with changes in sRNA levels with homology derived from the region.

As used herein term "reference", and the phrases "reference plant", "reference mammal", "reference organism", "reference methylome", or "reference genome" refer to a control organism, control genome, or control methylome that one or more experimental samples are being compared to, and wherein the control is or is derived from an organism lacking the features being selected in the experimental sample(s). A reference organism is chosen according to the purpose of the analysis and often is closely related but not displaying any phenotypes of interest. As such the reference organism's methylome generally lacks methylation patterns associated with phenotypes of interest such as a parental plant or progenitor of a parental plant prior to an epigenetic change, but otherwise isogenic to the candidate or test plant to which it is being compared.

As used herein, the term "wild-type" means "reference".

As used herein, the term "plant line" or "progeny" refers to any one of a first, second, third, or subsequent generation of progeny obtained from a parent plant if self-pollinated or from two parent plants if obtained from a cross, or to vegetatively propagated clones of the parent plant or plants. Multiple distinct plant lines can be obtained from the same parent or parents. Any materials of the plant, including seeds, tissues, pollen and cells can be used as sources of RNA or DNA for determining the status of the RNA or DNA composition of progeny.

As used herein, the phrases "suppression" or "suppressed" or "suppressing expression" of a gene refer to any genetic, nucleic acid, nucleic acid analog, environmental manipulation, grafting, transient or stably transformed methods of any of the aforementioned methods, or chemical treatment that provides for decreased levels of functional gene activity in a plant or plant cell relative to the levels of functional gene activity that occur in an otherwise isogenic plant or plant cell that had not been subjected to this genetic or environmental manipulation. Msh1 suppression of plasmidic Msh1 in the presence of mitochondrial-targeted Msh1 is also included as a form of suppression of Msh1.

As used herein, the phrases "increased DNA methylation" or "decreased DNA methylation" refer to nucleotides, regions, genes, chromosomes, and genomes located in the nucleus that have undergone a change in 5-methylcytosine levels in a plant or progeny plant relative to the corresponding parental chromosomal.

As used herein, the phrase "crop plant" includes cereal, seed, grain, fruit and vegetable crop plants.

As used herein, the term "F1" refers to the first progeny of two genetically or epigenetically different plants. "F2" refers to progeny from the self pollination of the F1 plant. "F3" refers to progeny from the self pollination of the F2 plant. "F4" refers to progeny from the self pollination of the F3 plant. "F5" refers to progeny from the self pollination of the F4 plant. "Fn" refers to progeny from the self pollination of the F(n−1) plant, where "n" is the number of generations starting from the initial F1 cross. Crossing to an isogenic line (backcrossing) or unrelated line (outcrossing) at any generation will also use the "Fn" notation, where "n" is the number of generations starting from the initial F1 cross.

As used herein, the terms "self", "selfing", or "selfed" refer to the process of self pollinating a plant.

As used herein, the term "S1" refers to a first selfed plant. "S2" refers to progeny from the self pollination of the S1 plant. "S3" refers to progeny from the self pollination of the S2 plant. "S4" refers to progeny from the self pollination of the S3 plant. "S5" refers to progeny from the self pollination of the S4 plant. "Sn" refers to progeny from the self pollination of the S(n−1) plant, where "n" is the number of generations starting from the initial S1 cross.

As used herein, the phrases "clonal propagate" or "vegetatively propagated" refer to a plant or progeny thereof obtained from a plant, plant cell, tissue, or seed that is propagated as a plant cutting or tuber cutting or tuber. Clonal propagates can be obtained by methods including regenerating whole plants from plant cells, plant embryos, cuttings, and tubers. Various techniques used for such clonal propagation include meristem culture, somatic embryogenesis, thin cell layer cultures, adventitious shoot culture and callus culture.

As used herein, the term "substantially" with reference to an equation, means that the equations agree within 10% at all relevant values, preferably within 5% at all relevant values, more preferably within 1% at all relevant values, and most preferably the equation agrees at all relevant values. As used in the case of preparing DIMPs and DIGRs, relevant values are those values used to determine if a methylated position in a genome is a DIMP, or used to determine if a genomic region is a DIGR.

As used herein, differentially informative methylated positions (DIMPs) are methylated genomic positions extracted from methylome data, which are selected for biological significance based on an approximation of the energy dissipated to produce a divergence between methylation levels of a sample as compared to a reference (such as a wild-type).

As used herein, differentially informative methylated region (DIMRs) are methylated genomic regions extracted from methylome data, which are selected for biological significance based on an approximation of the energy dissipated to produce a divergence between methylation levels of a sample as compared to a reference (such as a wild-type).

As used herein, discriminatory informative genomic regions (DIGRs) are regions of the genome of a plant or animal that carry information based on the DIMPs present in the genomic region and for which the pattern of methylation levels in the DIGRs are associated with the presence or absence of a characteristic of the organism.

As used herein, differentially expressed genes (DEGs) are the set of genes with a statistical significant amount of transcribed RNA which differ from a reference sample, at a specific time that reflects the current state of a cell or tissue.

As used herein, differentially expressed exons (DEEs) are the set of exons (coding regions in the genes) with a statistical significant amount of transcribed RNA which differ from a reference sample, at a specific time that can reflects differences in the expression of those genes with one or more isoforms.

As used herein, an organism (such as an animal or plant) is referred to as "harboring" a characteristic if the organism is not currently displaying the characteristic but will display the characteristic at a later stage of development. For example, a seed may harbor a characteristic for high yield, if when grown to a mature plant will display high yield.

DETAILED DESCRIPTION

Figure 1A:
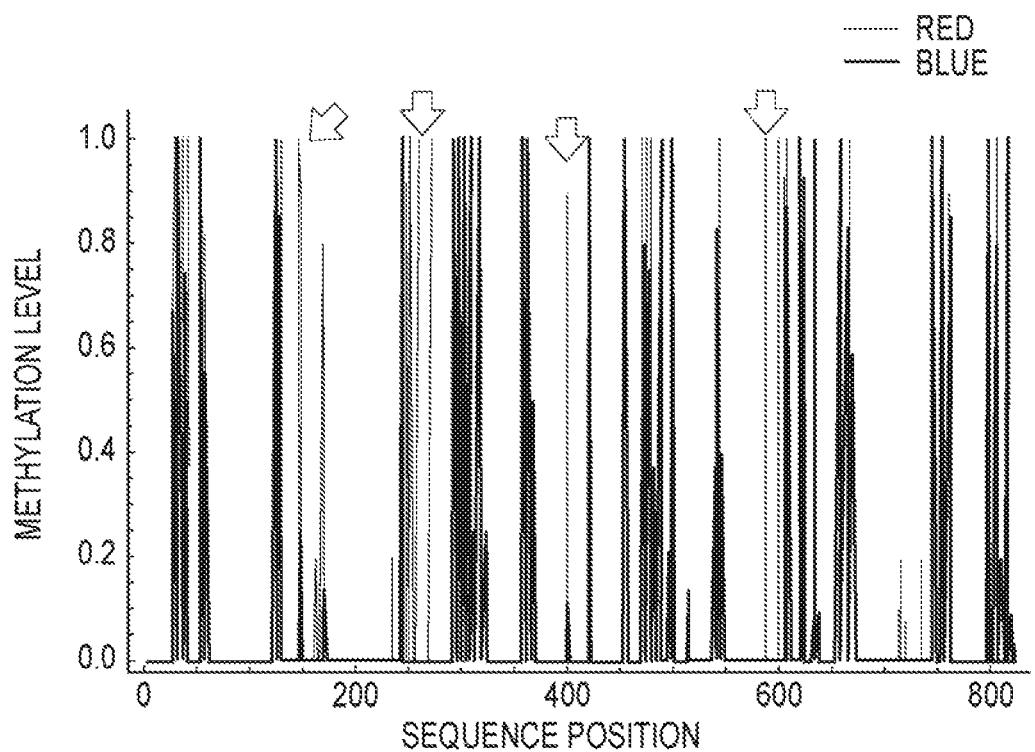
FIGS. 1A, 1B, 1C, 1D, 1E and 1F illustrates methylation profiles of annotated DIGRs for *Arabidopsis thaliana*.
Figure 1B:
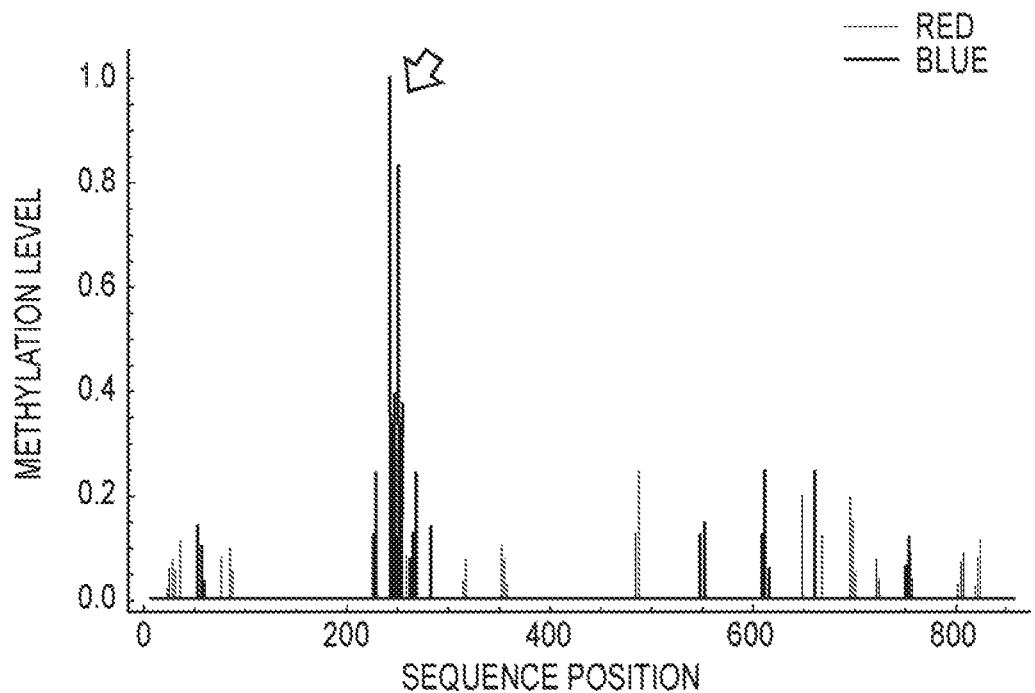
Figure 1C:
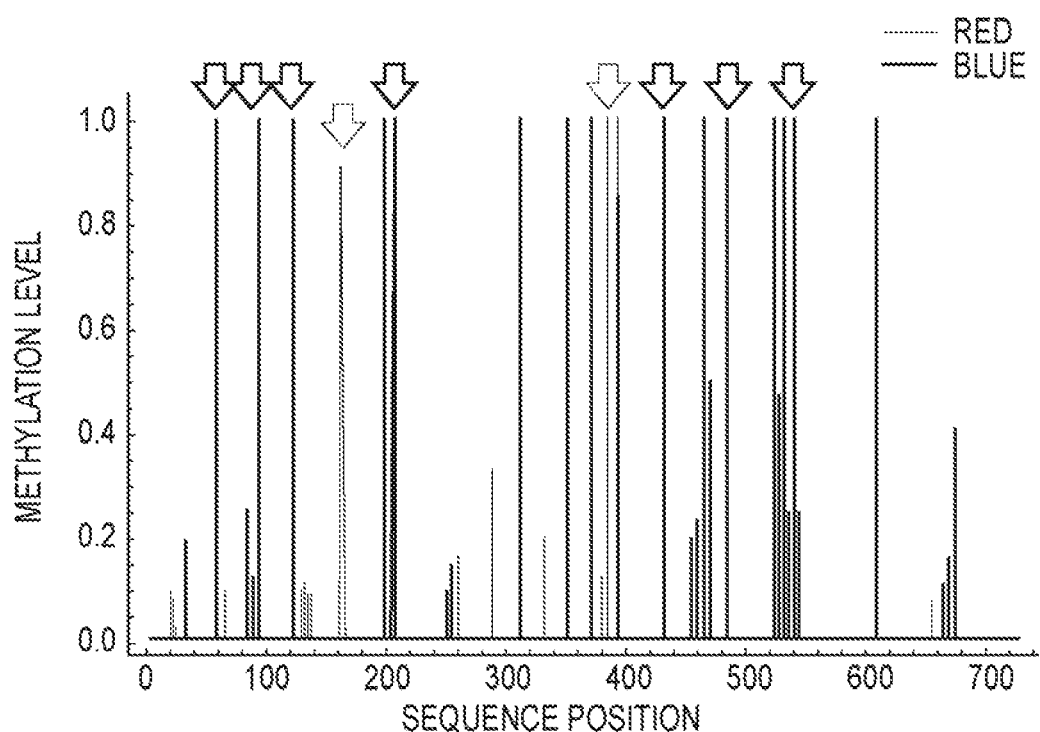
Figure 1D:
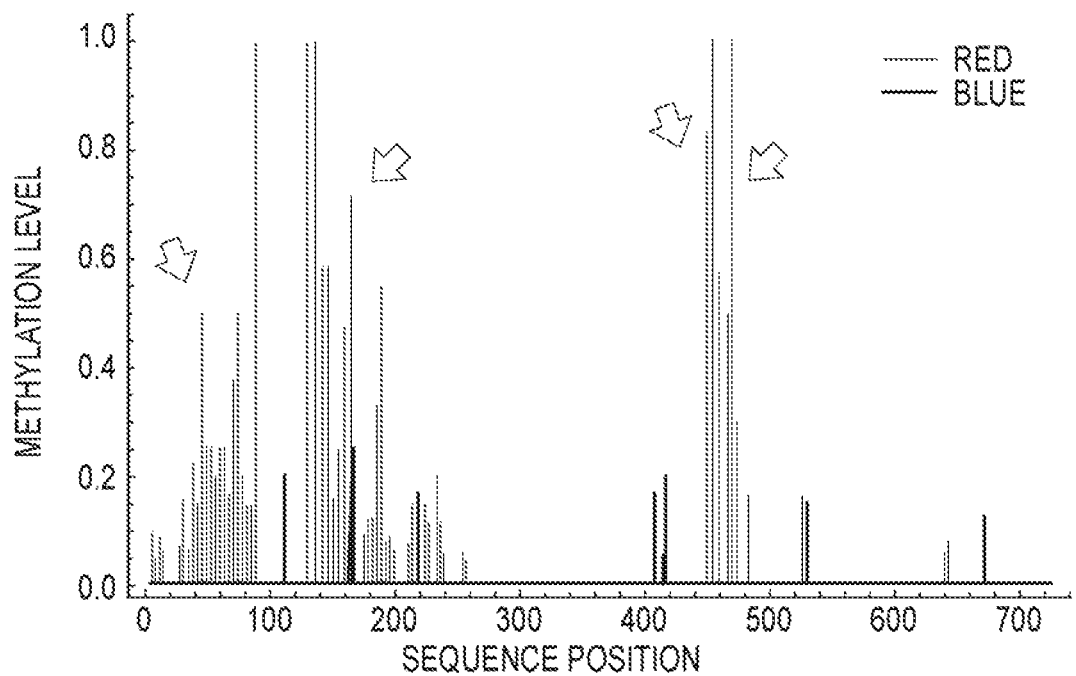
Figure 1E:
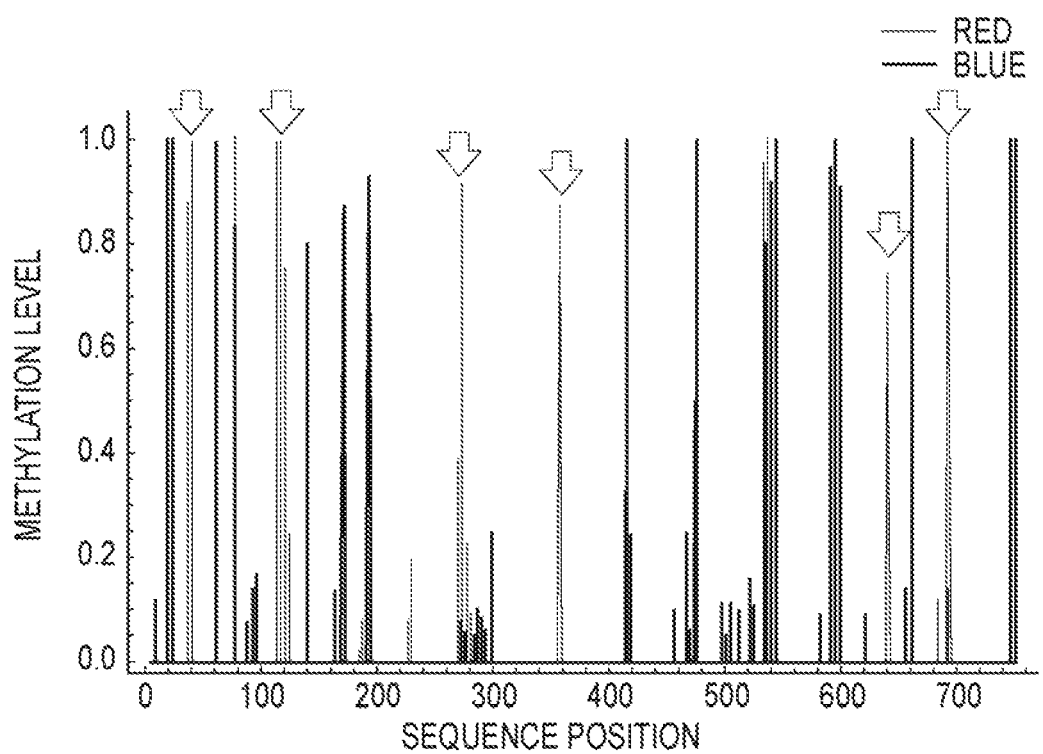
Figure 1F:
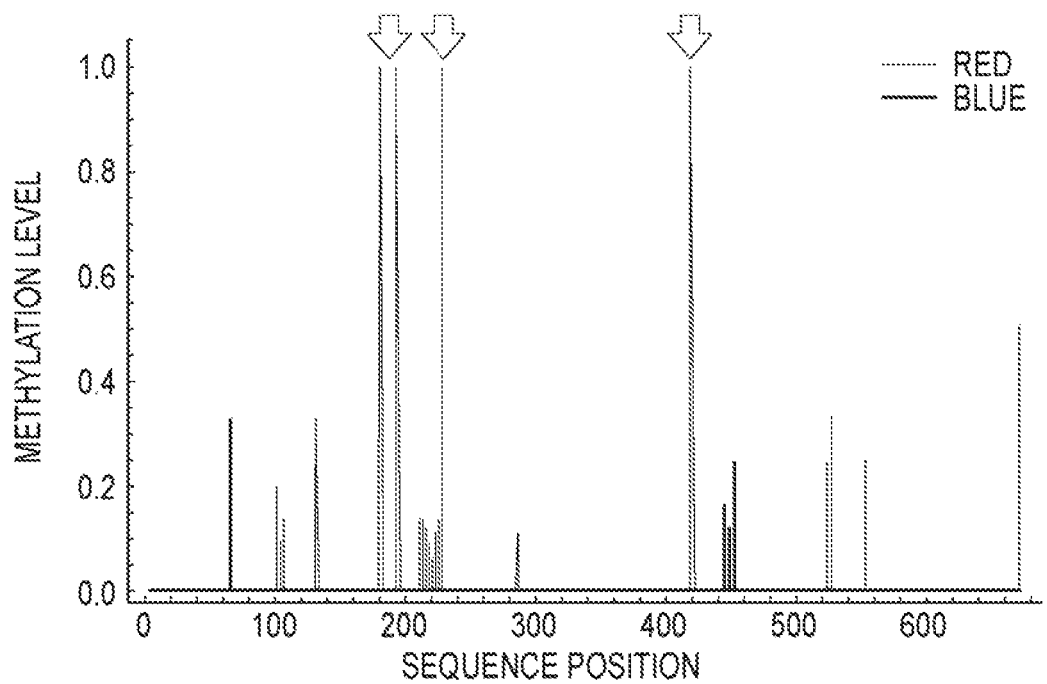

Two main sources of bias are present when DMPs are estimated by considering only the experimental data and a statistical test to evaluate the differences between samples. The first source of bias is introduced by ignoring the biophysical nature of the methylation process. A primary role of DNA methylation in animals and plants is the stabilization of DNA to prevent damage from thermal effects. Current statistical tests used to estimate DMPs fail to consider the statistical thermodynamics of DNA stabilization inherent to the methylation process. A second source of bias is introduced when a high number of multiple comparisons are performed. Adjustment of p-values is required for multiple comparisons and, in consequence, a number of potential DMPs can be rejected. Several algorithms and strategies have been proposed to confront this issue [27]. However, the application of these algorithms and strategies to detect DMPs can lead to subjective results.

The present invention provides an alternative approach to methylome analysis that considers the underlying information thermodynamic of the genome-wide methylation process to determine which methylation levels are biologically important. At a tissue level, methylated positions are the result of statistical-biophysical events that depend on the cells' capacities to perform physical work. Thus, the process for determining which methylated positions to include for methylome analysis selects methylated positions based on an objective difference that does not depend on the statistical test or the algorithm used to detect it, but rather the magnitude of energy dissipated to produce it. If the magnitude of the energy dissipated to produce an information-divergence associated with a methylation change is below a threshold of energy, then the methylation is for the stabilization of DNA and does not provide useful information.

The present invention makes use of differentially informative methylated positions (DIMPs) extracted from methylome data, which unlike DMPs are selected for biological significance based on an approximation of the energy dissipated to produce a information-divergence between methylation levels. For example, a DIMP detected by using a particular information-divergence measure in equation 5 (below) indicates that a statistically significant amount of energy was dissipated to produce it. But the amount of energy dissipated is relative to each tissue or individual. In addition, since the action of thermal fluctuations through the ontogenetic development of cells is not the same for every cell, DIMPs may differ between siblings of identical genetic background. These biophysical aspects of the methylation process may be addressed by the non-linear estimation of equation 8 for each individual, while these aspects are ignored by the application of statistical tests analogous or equivalent to Fisher's exact test used in current methylome analysis methods.

The resulting set of DIMPs effectively excludes those cytosine locations which are unlikely to correlate with phenotypic changes. The DIMPs may then be used in place of DMPs in existing methylome analyses techniques. Furthermore, the DIMPs may be used to produce a set of discriminatory informative genomic regions (DIGRs) that may be correlated with one or more phenotypic characteristics of the plant or animal. By examining methylome data obtained from a candidate seed, plant, or animal for these DIGRs, it can be predicted if the candidate seed, plant, or animal will likely express (or be unlikely to express) the associate phenotypic characteristic or characteristics.

The DIMPs, individually or grouped into combinations across genomic regions, are more likely to correlate with phenotypic differences due to differences in the methylome, than DMPs, allowing the identification of methylome patterns associated with phenotypic characteristics which may not be possible using DMPs. Also because of the greater likelihood of correlation, less computing time and less computing memory will be necessary to identify the correlations. These represent important technical advantage of the present invention.

The present invention also provides methods of analyzing DNA methylation patterns and using this information to identify which regions are associated with higher yields and/or stress tolerance in plants, to breed improved plants. The present inventions also provide a method to identify smaller subsets of DNA methylation signatures associated with improved agricultural performance in plants. This reduces the number of DNA methylation markers required to identify candidate plants with the potential for improved agricultural performance for traits affecting yield and/or stress tolerance. These same techniques can also be applied to animals and humans, to better diagnose diseases with an epigenetic contribution such as cancer and asthma.

Selection of Genomic Positions as DIMPs

Differentially informative methylated positions (DIMPs) are methylated genomic positions extracted from methylome data, which are selected for biological significance based on an approximation of the energy dissipated to produce a divergence between methylation levels of a sample as compared to a reference.

The addition or removal of a methyl group to a cytosine C5 residue produces a change of information that is recognized by the molecular transcription machinery and/or other proteins which recognize and respond to DNA methylation levels and changes. Shannon's entropy has been widely accepted as a measure of the uncertainty associated with random events [7]. The formula $$H(p(x_i)) = -p_i(x_i) \log_2 p(x_i) \qquad (Eq.\ 1)$$

of Shannon's entropy of a random event with probability distribution $p(x_i)$ can be applied to estimate the uncertainty (entropy) of the methylation events at a given cytosine site i as:

$$H(C_i) = -p(C_i)\log_2 p(C_i) - (1-p(C_i))\log_2(1-p(C_i)) \qquad (Eq.\ 2).$$

The entropy defined by Equation 2 is therefore the expected value of the logarithm base 2 of the methylation level [6]. An expression similar to Equation 2 was used in an experimental demonstration of information-to-energy conversion [8]. Furthermore, a modified expression of Equation 1 has been applied to quantitatively assess the variation in DNA methylation patterns [9].

When a change of methylation status in a genomic region R takes place, the absolute amount of information processed by the methylation machinery in the genomic region R is given by: $I_R = |\Sigma_{i \in R} H(C_i^{after}) - \Sigma_{i \in R} H(C_i^{before})|$ (Eq. 3), where $C_i^{before}$ and $C_i^{after}$ stand for the methylation status before and after, respectively. The absolute amount of information $I_R$ is defined as the absolute difference between two entropies (the uncertainty change) associated with the knowledge about two states (before and after) of a given system [3, 18, 19]. At tissue level, Equation 3 gives the uncertainty variation on the methylation status originated by the methylation changes at a given genomic region R or a single cytosine site. Thus, Equation 3 permits not only estimation of the uncertainty variation at a single cytosine position, but also the information-divergence $(D_R)$ between methylation levels, that is $D_R \cong I_R \cdot D_R$ is estimated as $D_R = \Sigma_{i \in R} D(p_i, q_i)$ (Eq. 4), where $D(p_i, q_i)$ is the divergence between the methylation levels $p_i$ and $q_i$ at a given cytosine site i inside of the region R, $i \in R$.

For example, a variety of information-theoretic measures of divergence $(D_R)$ may be used: Total-variation (TV), Kullback-Leibler (KL) and Hellinger ($H^D$) divergences. TV is the absolute value of the difference of methylation levels. KL gives the maximum information an observer could gain by observing a system [3], but still the extreme methylation change from 0 to 1 (and vice versa) has zero gain or loss of information. $H^D$ is an information divergence able to discriminate between all methylation levels. At a single cytosine position, $|\Delta p|$, KL and $H^D$ are computed by the expressions $$TV(p,q) = |p-q|,\ KL(p,q) = p\log\frac{p}{q} + (1-p)\log\frac{1-p}{1-q}$$

and $H^D(p,q) = (\sqrt{p}-\sqrt{q}+(\sqrt{1-p}-\sqrt{1-q})^2$, where p and q are the methylation levels at a single cytosine site. It is known that TV≤H$^D$≤KL≤$\chi^2$, where $\chi^2$ is the chi-squared divergence, also known as Pearson's chi-squared statistic. Any of these measures of divergence could may be used, but H$^D$ gives a conservative criterion about the divergence between the methylation levels, hence it was selected as the best choice. The magnitude of Hellinger divergence between the methylation levels may be evaluated at every single cytosine site according to the equation:

$$H^D(p_i, q_i) = (\sqrt{p_i} - \sqrt{q_i})^2 + (\sqrt{1-p_i} - \sqrt{1-q_i})^2 \quad (Eq. 5)$$

where $p_i$ and $q_i$ stand for the methylation levels observed at the genomic coordinate i of the methylome in the reference and query samples, respectively.

Differentially informative methylated positions (DIMPs) are extracted from methylome data, and unlike DMPs are selected based on an approximation of the energy dissipated to produce it. Let $F(E_k^D \leq E_k^{D_0})$ be the probability that energy $E_k^D$, dissipated to create an observed divergence $D_0$ between the methylation levels from two different samples at a given genomic position k, can be less than or equal to the observed amount of energy $E_k^{D_0}$. Then, a single genomic position k would be informative at a level of significance $\alpha$ if, and only if, the probability $F(E_k^D > E_k^{D_0}) = 1 - F(E_k^D \leq E_k^{D_0})$ to observe a methylation change with energy dissipation higher than $E_k^{D_0}$ is less than $\alpha$. This emphasizes the statistical-biophysical nature of methylated positions at tissue or cell level.

Based on simple assumptions, the probability density function (PDF) for the energies is approached by the Generalized Gamma distribution (GG), which is also known as Amoroso distribution [55a,55b]. The derivation of a GG distribution on a physical basis for the particular case of CDM is given in the Appendix [56]. A GG distribution is a flexible distribution in statistical literature, and has exponential, gamma, and Weibull as subfamilies, and log normal as a limiting distribution. This is also borne out by observation. According to Landauer's principle, a methyltransferase or demethylase must dissipate at least a minimum energy of $\varepsilon = k_B T \ln 2$ (about $3 \times 10^{-21}$ Joules at room temperature) at each step in the genetic logic operations including proofreading [3,4]. This is the expected minimal energy dissipation that a molecular machine must spend to produce a change in one bit of information. Therefore, under Landauer's principle, the minimum energy dissipated to process the information $I_R$ can be approached by the equation: $E_R = I_R k_B T \ln 2$. In consequence, under Landauer's principle, the PDF of the information $I_R$ is also a GG distribution:

$$f(I_R | \alpha, \lambda, \mu, \psi) = \frac{\alpha}{\lambda(l)\Gamma(\psi)} \left(\frac{I_R - \mu}{\lambda(l)}\right)^{\psi\alpha - 1} e^{-\left(\frac{I_R - \mu}{\lambda(l)}\right)^\alpha}, I_R > \mu > 0, \quad (Eq. 6)$$

with location parameter $\mu$, a scale parameter $\lambda(l)$, and two shape parameters, $\alpha$ and $\psi$. In particular, in our application $\lambda(l) = \varphi(l)/\ln 2$, where $\varphi(l)$ expresses the contribution of all degrees of freedom to the average energy per molecule as a function of genomic region length l. Some properties of GG useful for our application are given in reference [57]. An extensive list of GG distributions is given in references [55b,58].

Depending on the experimental sample, GG distribution as well as several members of its family, such as 3-parameters Gamma and Weibull distributions are found in the goodness of fits of CDM data. In particular, the more frequent member from this family found in the fitting of genome-wide single CDM is Weibull distributions with PDF:

$$f(I_R | \alpha, \lambda, \mu) = \frac{\alpha}{\lambda(l)} \left(\frac{I_R - \mu}{\lambda(l)}\right)^{\alpha - 1} e^{-\left(\frac{I_R - \mu}{\lambda(l)}\right)^\alpha}, I_R > \mu > 0, \quad (Eq. 7)$$

which derives from Eq. 6 when $\psi = 1$. Preferably, a Weibull distribution is used. Recognizing that $D_R \cong I_R$, a particular information-divergence measure $D_R$ (like any of those mentioned above) has GG distribution, provided that $D_R$ is proportional to $E_R^D$. In particular, $D_R \cong H_k^D$ results in cumulative distribution function (CDF):

$$F(H_R^D | \hat{\alpha}, \hat{\mu}, \hat{\lambda}(l), \hat{\psi}) = \begin{cases} \frac{1}{\Gamma(\hat{\psi})} \gamma\left(\hat{\psi}, \left(\frac{H_R^D - \hat{\mu}}{\hat{\lambda}(l)}\right)^{\hat{\alpha}}\right) & \hat{\psi} > \hat{\mu} > 0 \\ 1 - \frac{1}{\Gamma(\hat{\psi})} \gamma\left(\hat{\psi}, \left(\frac{H_R^D - \hat{\mu}}{\hat{\lambda}(l)}\right)^{\hat{\alpha}}\right) & \hat{\psi} \leq 0 \end{cases}, \quad (Eq. 8)$$

where $\gamma$ is the incomplete Gamma function and the parameter values $\hat{\alpha}$, $\hat{\mu}$, $\hat{\lambda}(l)$ and $\hat{\psi}$ are estimations of the theoretical parameters obtained from the non-linear fit of experimental methylome data (symbol "^" indicates that a value is estimated from the experimental data). Equation 8 may be used to compute $\alpha_0^k = 1 - \hat{F}(H_k^D \leq H_k^{D_0} | \hat{\alpha}, \hat{\mu}, \hat{\lambda}, \hat{\psi})$ at each cytosine position k (R=k) replacing $H_k^{D_0}$ by the corresponding estimated $H_k^{D_0}$ value. That is, $F(E_k^D \leq E_k^{D_0} | \alpha, \eta, \beta, \psi) \cong F(H_k^D \leq H_k^{D_0} | \alpha, \mu, \lambda, \psi)$, provided that $H_k^D$ is proportional to $E_k^D$ at each single cytosine position k, where $\beta$ and $\eta$ are model parameters analogous to $\lambda$ and $\mu$, but given in energy units.

A single genomic position k is a DIMP at a level of significance $\alpha$ if, and only if, the probability $\alpha_0^k$ to observe a methylation change with Hellinger divergence $H_k^D$ higher than $H_k^{D_0}$ is less than $\alpha$ ($\alpha_0^k \leq \alpha$). $\alpha$ is at most 0.10, and preferably $\alpha$ is 0.07, more preferably $\alpha$ is 0.05. This definition can also be given in terms of any other information divergence measure that could be relevant for specific methylome data set.

Each methylome sample has its corresponding estimation of $\hat{F}(H_k^D \leq H_k^{D_0} | \alpha, \mu, \lambda, \psi)$. That is, the estimation of DIMRs (or DIMPs, R=k) is particularized for each sample and the parameter values of Equation 8 estimated for a sample will depend on the individual methylome data set. Since Equation 8 takes into account the methylation changes induced by thermal fluctuations, methylation changes reported as DMPs by the "classical methods" will not necessarily be DIMPs according to Equation 8. In effect, using DIMPs instead of DMPs to analyze methylome data will improve the correlation of methylome data with phenotypic characteristics which are affected by methylation.

The application of GG distribution to fit genome wide single CDM is computational expensive and may not be practical for the typical computer hardware found in many molecular biology laboratories. In such a case, a sampling experiment with several methylomes from *Arabidopsis thaliana* indicates that a Weibull CDF $$\hat{F}(H_k^D \leq H_k^{D_0} | \hat{\alpha}, \hat{\lambda}, \hat{\mu}) = 1 - e^{-\left(\frac{H_k^{D_0} - \hat{\mu}}{\hat{\lambda}(l)}\right)^{\hat{\alpha}}}, \quad (Eq. 9)$$

which derives from GG PDF via Eqs. 6 and 7 (by using $H_R^D$ in place of $I_R$), yields a conservative estimation of DIMPs based on $\alpha_0^k = 1 - \hat{F}(H_k^D \leq H_k^{D_0})$ (Table 1). However, as suggested in Table 1, to find which member of GG distribution family yields the best fit for each particular methylome sample would increase the sensitivity of DIMP detection.

TABLE 1

DIMPs counts in 5000 random samplings of size 10000 bp each. Non-linear fits of the general gamma and Weibull distributions were performed after each one of the 5000 samplings in each methylome sample. The raw data correspond to the 30th generation of trans-generational studies from reference [15]. AIC: Akaike Information Criterion.

|  | L119R1 | | | L119R2 | | | L19R1 | | |
|---|---|---|---|---|---|---|---|---|---|
|  | Quantile 0.25% | Mean | Quantile 0.75% | Quantile 0.25% | Mean | Quantile 0.75% | Quantile 0.25% | Mean | Quantile 0.75% |
| General Gamma distribution (GG) | 634 | 646.0 | 658 | 668 | 678.6 | 696 | 608 | 620.0 | 633 |
| 3 parameter Weibull distribution (3P-W) | 616 | 629.9 | 649 | 673 | 685.4 | 700 | 593 | 606.0 | 626 |
| Empirical Commutative Distribution Function (ECDF) | 502 | 514.4 | 521 | 500 | 512.0 | 519 | 500 | 514.8 | 510 |
| Intersection GG & 3P-W | 616 | 629.7 | 649 | 668 | 678.6 | 696 | 593 | 605.5 | 626 |
| Intersection GG & ECDF | 502 | 514.4 | 521 | 500 | 512.0 | 519 | 500 | 514.8 | 510 |
| Intersection 3P-W & ECDF | 502 | 514.4 | 521 | 500 | 512.0 | 519 | 500 | 514.7 | 510 |
| Intersect GG & 3P-W & ECDF | 502 | 514.4 | 521 | 500 | 512.0 | 519 | 500 | 514.7 | 510 |
| GG.AIC | −136364 | −136364 | −136364 | −155398 | −155398 | −155398 | −146762 | −146762 | −146762 |
| 3P-W.AIC | −136349 | −136349 | −136349 | −153360 | −153360 | −153360 | −146623 | −146623 | −146623 |
| GG.Residual Sum Of Squares | 6.26E−04 | 6.92E−04 | 7.53E−04 | 1.39E−04 | 1.61E−04 | 1.79E−04 | 2.71E−04 | 3.06E−04 | 3.38E−04 |
| 3P-W.Residual Sum Of Squares | 6.46E−04 | 7.21E−04 | 7.89E−04 | 1.74E−04 | 2.01E−04 | 2.25E−04 | 2.76E−04 | 3.15E−04 | 3.49E−04 |

|  | L19R2 | | | L29R1 | | | L29R2 | | |
|---|---|---|---|---|---|---|---|---|---|
|  | Quantile 0.25% | Mean | Quantile 0.75% | Quantile 0.25% | Mean | Quantile 0.75% | Quantile 0.25% | Mean | Quantile 0.75% |
| General Gamma distribution (GG) | 636 | 649.2 | 666 | 635 | 646.4 | 658 | 607 | 618.5 | 630 |
| 3 parameter Weibull distribution (3P-W) | 574 | 610.6 | 645 | 622 | 635.7 | 652 | 599 | 612.6 | 627 |
| Empirical Commutative Distribution Function (ECDF) | 506 | 521.0 | 532 | 502 | 513.9 | 519 | 500 | 519.9 | 516 |
| Intersection GG & 3P-W | 574 | 610.3 | 645 | 621.75 | 635.4 | 651 | 599 | 612.0 | 627 |
| Intersection GG & ECDF | 506 | 521.0 | 532 | 502 | 513.9 | 519 | 500 | 519.9 | 516 |
| Intersection 3P-W & ECDF | 506 | 521.0 | 532 | 502 | 513.9 | 519 | 500 | 519.9 | 516 |
| Intersect GG & 3P-W & ECDF | 506 | 521.0 | 532 | 502 | 513.9 | 519 | 500 | 519.9 | 516 |
| GG.AIC | −142677 | −142677 | −142677 | −136650 | −136650 | −136650 | −142255 | −142255 | −142255 |
| 3P-W.AIC | −142647 | −142647 | −142647 | −136570 | −136570 | −136570 | −141596 | −141596 | −141596 |
| GG.Residual Sum Of Squares | 4.59E−04 | 5.11E−04 | 5.59E−04 | 6.64E−04 | 7.35E−04 | 8.00E−04 | 3.39E−04 | 3.81E−04 | 4.19E−04 |
| 3P-W.Residual Sum Of Squares | 4.75E−04 | 5.33E−04 | 5.85E−04 | 6.80E−04 | 7.58E−04 | 8.29E−04 | 3.45E−04 | 3.89E−04 | 4.27E−04 |

|  | L49R1 | | | L49R2 | | | L59R1 | | |
|---|---|---|---|---|---|---|---|---|---|
|  | Quantile 0.25% | Mean | Quantile 0.75% | Quantile 0.25% | Mean | Quantile 0.75% | Quantile 0.25% | Mean | Quantile 0.75% |
| General Gamma distribution (GG) | 643 | 658.9 | 672 | 591 | 607.6 | 619 | 636 | 648.6 | 662 |
| 3 parameter Weibull distribution (3P-W) | 636 | 650.4 | 665 | 591 | 609.8 | 622 | 613.75 | 628.1 | 651 |
| Empirical Commutative Distribution Function (ECDF) | 501 | 557.5 | 606 | 536 | 550.3 | 567 | 503 | 516.0 | 524 |
| Intersection GG & 3P-W | 636 | 650.0 | 664 | 589 | 604.8 | 617 | 613 | 627.9 | 651 |
| Intersection GG & ECDF | 501 | 557.6 | 606 | 536 | 550.3 | 567 | 503 | 516.0 | 524 |
| Intersection 3P-W & ECDF | 501 | 557.5 | 606 | 536 | 550.3 | 567 | 503 | 516.0 | 524 |
| Intersect GG & 3P-W & ECDF | 501 | 557.6 | 606 | 536 | 550.3 | 567 | 503 | 516.0 | 524 |
| GG.AIC | −133646 | −133646 | −133646 | −145447 | −145447 | −145447 | −136893 | −136893 | −136893 |
| 3P-W.AIC | −133182 | −133182 | −133182 | −145439 | −145439 | −145439 | −135881 | −135881 | −135881 |
| GG.Residual Sum Of Squares | 7.41E−04 | 4.85E−01 | 8.90E−04 | 3.13E−04 | 3.51E−04 | 3.87E−04 | 5.54E−04 | 6.16E−04 | 6.73E−04 |
| 3P-W.Residual Sum Of Squares | 7.55E−04 | 8.39E−04 | 9.13E−04 | 3.16E−04 | 3.55E−04 | 3.90E−04 | 5.72E−04 | 6.40E−04 | 7.02E−04 |

|  | L59R2 | | | L69R1 | | | L69R2 | | |
|---|---|---|---|---|---|---|---|---|---|
|  | Quantile 0.25% | Mean | Quantile 0.75% | Quantile 0.25% | Mean | Quantile 0.75% | Quantile 0.25% | Mean | Quantile 0.75% |
| General Gamma distribution (GG) | 575 | 595.4 | 608 | 602 | 629.4 | 660 | 580 | 611.5 | 644 |
| 3 parameter Weibull distribution (3P-W) | 573 | 594.3 | 607 | 600 | 629.5 | 663 | 569 | 597.6 | 631 |
| Empirical Commutative Distribution Function (ECDF) | 517 | 533.6 | 548 | 536 | 550.7 | 567 | 510 | 525.5 | 538 |
| Intersection GG & 3P-W | 571 | 589.9 | 602 | 597 | 621.4 | 646 | 568 | 594.2 | 623 |
| Intersection GG & ECDF | 517 | 533.6 | 548 | 536 | 550.7 | 567 | 510 | 525.5 | 538 |
| Intersection 3P-W & ECDF | 517 | 533.6 | 548 | 536 | 550.7 | 567 | 510 | 525.5 | 538 |
| Intersect GG & 3P-W & ECDF | 517 | 533.6 | 548 | 536 | 550.7 | 567 | 510 | 525.5 | 538 |
| GG.AIC | −146490 | −146490 | −146490 | −139717 | −139717 | −139717 | −143459 | −143459 | −143459 |
| 3P-W.AIC | −146492 | −146492 | −146492 | −139719 | −139719 | −139719 | −143171 | −143171 | −143171 |
| GG.Residual Sum Of Squares | 2.29E−04 | 2.59E−04 | 2.87E−04 | 4.72E−04 | 5.24E−04 | 5.74E−04 | 2.75E−04 | 3.11E−04 | 3.43E−04 |
| 3P-W.Residual Sum Of Squares | 2.32E−04 | 2.62E−04 | 2.90E−04 | 4.77E−04 | 5.30E−04 | 5.79E−04 | 2.78E−04 | 3.15E−04 | 3.48E−04 |

As an example, a set of DIMPs (that is, a set of differentially informative methylated positions) may be produced from methylome data of a sample and methylome data of a wild-type, as follows:

First, compute the Hellinger distance ($\hat{H}_k^{D_0}$) between the sample and the wild-type at each cytosine position k in the methylomes according to Equation 5.

Second, perform a non-linear fit of Equation 9 (by using a non-linear regression analysis) of the empirical cumulative distribution function (ECDF, denoted as $\hat{F}_n(H_k^D \leq \hat{H}_k^{D_0})$) estimated for the variable $\hat{F}_n(H_k^D \leq \hat{H}_k^{D_0})$ versus $\hat{H}_k^{D_0}$, to get an estimation of $\hat{F}_n(H_k^D \leq \hat{H}_k^{D_0} | \hat{\alpha}, \hat{\mu}, \hat{\lambda})$. The ECDF of the variable $\hat{H}_k^{D_0}$ is defined as:

$$\hat{F}(H_k^D \leq \hat{H}_k^{D_0}) = \qquad (\text{Eq. 10})$$

$$\frac{\text{number of } CDMs \text{ in the samples with } H_k^D \leq \hat{H}_k^{D_0}}{n} =$$

$$\frac{1}{n} \sum_{k=1}^{n} 1_{H_k^D \leq \hat{H}_k^{D_0}}$$

$$\text{where } 1_{H_k^D \leq \hat{H}_k^{D_0}} = \begin{cases} 1 \text{ if } H_k^D \leq \hat{H}_k^{D_0} \\ 0 \text{ if } H_k^D > \hat{H}_k^{D_0} \end{cases},$$

is the indicator function. Function $\hat{F}_n(H_k^D \leq \hat{H}_k^{D_0})$ is easily computed (for example, by using function "ecdf" of the statistical computing program "R" [32]). This will also give values for $\hat{\alpha}, \hat{\mu}$ and $\hat{\lambda}$.

Third, use the $\hat{F}_n(H_k^D \leq H_k^{D_0} | \hat{\alpha}, \hat{\mu}, \hat{\lambda})$ CDF to compute $\alpha_0^k = 1 - \hat{F}_n(H_k^D \leq H_k^{D_0} | \hat{\alpha}, \hat{\mu}, \hat{\lambda})$ at each cytosine position k by replacing $H_k^{D_0}$ by the corresponding $\hat{H}_k^{D_0}$ estimated value in the last equation.

Fourth, create a set of DIMPs at a level of significance $\alpha$ for the sample methylome data by only including those cytosine positions where the probability $\alpha_0^k$ to observe a methylation change with Hellinger divergence $H_k^D$ higher than $H_k^{D_0}$ is less than $\alpha$ ($\alpha_0^k \leq \alpha$). $\alpha$ is at most 0.10, and preferably $\alpha$ is 0.07, more preferably $\alpha$ is 0.05.

For each methylome, the parameters of Equation 9 may be estimated by applying the Levenberg-Marquardt nonlinear least-squares algorithm available in "R" package minpack.lm [32]. Cross-validations for the nonlinear regressions may be performed in each methylome as previously described [36]. In addition, Stein's formula for adjusted R squared ($R_{Adj}^2$) was used as an estimator of the average cross-validation predictive power.

Other measures of divergence may be used, such as Total-variation (TV), Kullback-Leibler variance (KL), or where $\lambda^2$ is the chi-squared divergence. Other distribution functions may be used instead of a Weibull distribution, for example other exponential distribution functions, any member of the GG distribution family or the first 3, 4 or 5 terms of a Taylor polynomial expansion of a GG distribution. However, the best model is preferably selected on the bases of its values of Akaike [59] or Bayesian information criteria (denoted AIC and BIC respectively), provided that model parameter values estimated from the experimental data are consistent with their statistical mechanical meaning (preventing numerical artifacts).

As presented in Table 1, function $\hat{F}_n(H_k^D \leq H_k^{D_0})$ (or $\hat{F}_n(H_k^D \leq H_k^{D_0})$) can also be used to perform a full empirical estimation of DIMPs (or DIMRs) by setting $\alpha_0^k = 1 - \hat{F}_n(H_k^D \leq H_k^{D_0})$ (or $\alpha_0^R = 1 - \hat{F}_n(H_k^D \leq H_k^{D_0})$). However, the sensitivity to select DIMPs depends on the statistical mechanical based family of GG distribution. $\hat{F}_n(H_k^D \leq H_k^{D_0})$ ($\hat{F}_n(H_k^D \leq H_k^{D_0})$) does not control the errors from the experimental data.

Partition of the Methylome into Regions

The whole genome or a subset of the genome may be split into N regions $R_s$. In each genomic region (GR), the information-divergence $D_R$ between the reference (control) and the query samples are estimated. Now each plant methylome is represented as a vector of N $D_R$ variables.

A variety of subsets into which the methylome may be split is possible, such as variable length or fixed length. Examples of natural partitions into subsets of variable length are the annotated genomic features such as transcripts, exon, introns, etc. An algorithmic approach to split the methylome into subsets of potential word framework (PWF) is presented in [63]. A particular example of partition into subsets of fixed length is the set of all single cytosines found in a given methylome. In this case $D_R = D_k$, that is, R=k.

Selection of Genomic Regions as DIMRs

The approach described above to detect DIMPs can be extended to detect differentially informative methylated regions (DIMRs). A genomic region R shall be called a DIMR at a level of significance $\alpha$ if, and only if, the probability $\alpha_0^R$ to observe a methylation change with Hellinger divergence $H_R^D$ higher than $H_R^{D_0}$ is less than $\alpha$ ($\alpha_0^R \leq \alpha$). $\alpha$ is at most 0.10, and preferably $\alpha$ is 0.07, more preferably $\alpha$ is 0.05.

The same steps described to select DIMPs are followed, but now performing a non-linear fit of Equation 9 for $\hat{H}_k^{D_0}$ estimated for in each region from a set of genomic regions. This step will yield the functionals $\hat{F}_n(H_k^D \leq H_k^{D_0} | \hat{\alpha}, \hat{\mu}, \hat{\lambda})$ and $\alpha_0^R = 1 - \hat{F}_n(H_k^D \leq H_k^{D_0} | \hat{\alpha}, \hat{\mu}, \hat{\lambda})$, which will be used to estimate the DIMRs by replacing $H_k^{D_0}$ by the estimated value $H_k^{D_0}$ at each genomic region R. The GRs used in non-linear fit of Equation 9 derives from some partition of the methylome into N regions (as described in the previous section).

Selection of Genomic Regions as DIGRs

To accomplish the classification of plant or animal phenotypes based on their methylomes, the whole genome or a subset of the genome may be split into N regions $R_s$ as described above, and each plant methylome is represented as a vector of N $D_R$ variables.

The search for DIGRs is not attached to a particular partition. In fact, the combination of the results derived from different partitions increases the confidence in the method's predictions. Under the absence of any external information about the relationship between methylation and phenotypes, a preferable set to start, which is used in the following description, is a partition of the genome into non-overlapped regions R of n base pairs, for example of 2,000 base pairs each.

The detection of differentially informative genomic regions (DIGRs) is accomplished, for example, based on a heuristic and the application of Equation 4, but the sum is only run over the DIMPs, (rather than every single cytosine position). Furthermore, $D(p_i, q_i)$ is selected as the Hellinger distance ($H^D(p_i, q_i)$, equation 5), so $H_R^D = \Sigma_{i \in R} H_D(p_i, q_i)$. Accordingly, each methylome is a vector in N-dimensional metric space $R^N$ of N $H_R^D$ variables.

The heuristic includes the following subsequent steps:

(1) A prior classification of the individuals is proposed and provided for the linear discriminant analysis (LDA). A matrix of individual methylomes, represented as vectors in the N-dimensional metric space $R^N$ of N $H_R^D$ variables, can be visualized in a heat-map graph. Normally, heat-maps of the $H_R^D$ variables permit visually the grouping of the individuals into big "obvious" sets, which can be used as prior classification (in step 1, see FIG. 2). This knowledge together with any potential external information about the relationship of methylation versus phenotype will reduce the number of possible prior classifications to test in the downstream analysis.

(2) Principal component analysis (PCA) is applied to reduce the dimensionality of the space performing feature extraction. The number of principal components (PCs) included in further steps is based the fraction of the whole sample variance carried by the PCs. Preferably it is requested that the selected PCs must carry at least the 70% of the whole sample variance (feature extraction step).

(3) The selected PCs are used as new variables in the LDA analysis.

(4) An iterative cross-validation process is carried out. At each step m ten-fold cross validations are performed to look for the prior classification used in step 1 that produces the maximum classification accuracy. The posterior classification derived from the LDA with maximum classification accuracy is considered the right classification of the set of individuals under consideration. An accuracy of no less than 70% is demanded and preferably an accuracy of 80%, more preferably 90%, and most preferably 95% or more is demanded.

(5) A feature selection step is performed based on the contributions of original variables to the principal components. Then, a subset of GRs with the major contribution to the PCA is selected to produce a set of DIGRs which can identify the phenotypic characteristic based on a methylome; preferably steps 2 to 5 are repeated with the extracted DIGRs until the minimal subset of DIGRs is found which is able to classify the whole set of individuals with the maximum classification accuracy, which must be no less than the classification accuracy obtained for the whole set of DIGRs. This will produce the smallest set of DIGRs which can identify the phenotypic characteristic based on a methylome.

It is also possible to carry out the heuristic using support vector machine (SVM) or a suitable machine learning approach instead of LDA, or in fact any available de novo classifier algorithm. Similarly, it is also possible to carry out the heuristic using machine learning instead of PCA, or in fact any other type of factor analysis (FA). LDA and PCA may be carried out, for example, using R-package "adegenet" [41]. SVM and various machine learning algorithms are available in the computer program WEKA [42].

If the number of GRs is lesser than the number of individuals ($n_i$) divided by 3, i.e., if $N \leq n_i/3$, alternative methods can be applied in place of the PCA (FA) step. For example, logistic regression (for the classification into two sets of individual phenotypes) or multinomial logistic regression (for the classification of into three or more sets of individual phenotypes). In these cases, the contribution of the GRs to the classification is evaluated based on the analysis of the regression coefficients. In the case of the classification into two sets of individual phenotypes, logistic regression and LDA are mathematically equivalent. For the classification of into three or more sets of individual phenotypes, LDA can be applied directly to the original variables, which combined with multinomial logistic regression will give a robust estimation of the DIGRs. The application of the heuristic to different methylome partitions and/or the use of external information about the relationship methylation versus phenotype may reduce the set of GRs of biological interest to a number $N \leq n_i/3$.

Figure 2:
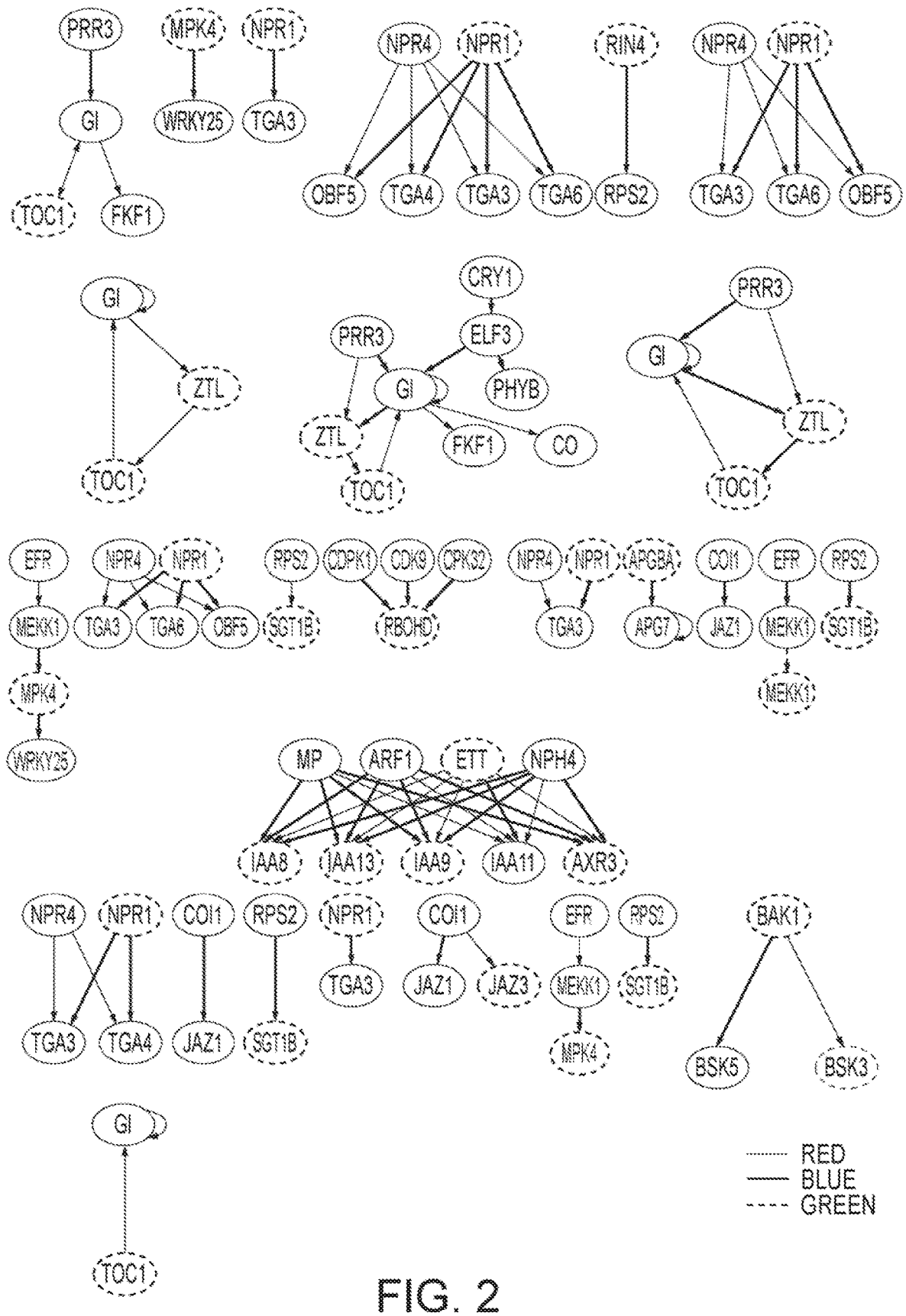
FIG. 2 is an illustration of a gene graph enrichment analysis for significant pathways involving genes with DEEs-splicing-junctions carrying DIMPs in Epi-lines plants.

Alternatively, in many cases the DIGRs will be immediately apparent from a comparison of graphs of genomic regions and the density of DIGRs (also referred to as heat-maps), as shown in FIG. 2. Such visual comparisons may also be used as a starting classification to carry out the heuristic described above.

Selection of Seeds, Plants or Animals with Phenotypic Characteristics Associated with Methylome Differences DIGR detection is useful for the identification of epigenetic quantitative trait loci (epiQTL, or expression quantitative trait loci or eQTL). That is, the DIGRs are genomic regions carrying a fraction of the whole sample of individual variance associated to the individual phenotypes. Each DIGR carries one or more DIMPs, which constitute a sort of fingerprint for the given region. The comparison of the DIGRs with differentially expressed genes (DEGs) data will reveal whether or not the adherence to a specific discriminatory methylation pattern observed in a DIGR is associated to the differential expression of a gene linked to the detected DIGR. Such a DIGR will be considered an epiQTL. A further step will consider the biochemical pathway and gene ontology enrichment analyses of the detected epiQTL(s).

The combination of DIGRs with DIMRs could increase the sensitivity of the method. In particular, the heuristic to detect DIGRs can be run only over the previously detected DIMRs.

An important application of the method is the detection of DIGRs in epigenetically induced reprogramming of individual plants. For example, the detection of DIGRs in epigenetically induced reprogrammed plants obtained by using Msh1 suppression as described in U.S. Pat. App., Pub. No. US 2012/0284814 to Mackenzie et al. or U.S. Pat. App., Pub. No. US 2015/0113679 to Mackenzie et al.

Several diseases, for example cancer and asthma, and a complex disorder like obesity, are associated with spontaneous abnormal epigenetic reprogramming. The application of these methods allows for the identification of the DIGRs involved in the manifestations of these diseases, which may be used as epigenetic biomarkers.

Once DIGRs associated with a phenotypic characteristic have been identified for an animal or plant, they may be used to identify other members of the species which are likely to exhibit the same characteristic, or to identify other members of the species which are unlikely to exhibit the same characteristic. For example, DIGRs may be used to screen sibling plants for DNA methylation patterns indicative of those most likely to harbor useful agronomic traits such as higher yield potential and higher stress tolerance potential. A tissue sample may be obtained from the plant or animal, for example a chip from a seed, a tissue of a plant, or a sample of blood or a tissue biopsy from an animal. Then, the methylome of the sample may be determined by any one of various known methods, for example using DNA bisulfite conversion methodology coupled with next-generation sequencing approaches (Bis-seq), or alternatively other region-specific methods that distinguish C and T (or complementary G and A) nucleotides as specific positions to detect DNA methylation at a subset of the genome may be used. Then the methylation levels (or methylome) of the sample may be examined for the DIGRs associated with a trait or traits: if the DIGRs are present, then the plant or animal from which the sample was taken is likely to exhibit the characteristic. Similarly, if the methylome is missing some or most of the DIGRs, then the plant or animal from which the sample was taken is less likely to exhibit the characteristic. For example, cells or tissue from seeds (such as the endosperm, embryo cells or embryo tissue) may be examined to determine the methylome of the tissue and the presence of DIGRs associated with a characteristic of interested (such as high growth rate), allowing for the selection of seeds carrying the characteristic associated with the DIGRs without having to grow the seed, potentially greatly reducing the number of seed which would have to be grown into plants to obtain a collection of plants having the selected characteristic. Seed chippers, including high speed seed chippers, may be used to obtain tissue samples from seeds. Similarly leaves or other plant tissue could also be used to identify plants harboring desirable characteristics.

A large variety of techniques are available for determining the methylome of animals and plants, any of which may be used with the present invention [50, 51]. A methylome may also be prepared from targeted genomic regions associated with small RNAs that are up or down regulated in the sample plants (in comparison to control or reference plants). This method is based in part on identification of small interfering RNAs that direct or maintain DNA methylation of specific genome targets by RNA-directed DNA methylation (RdDM). The RNA-directed DNA methylation (RdDM) process has been described [52]. A variety of techniques are available to compare small RNAs in the test and reference plants, any of which may be used with the present invention to identify a subset of genome regions for obtaining DNA methylation measurements and for DIGR analysis by the methods herein [53].

Comparison of methylomes to determine the presence of common DIMPs, DIMRs, and DIGRs may be carried out by visual comparison (for example by comparing heat maps such as those of FIG. 4 and FIG. 5), or by a detailed examination of the methylation level of each relevant cytosine position. Preferably, at least 50%, 60%, 70%, 80%, 90%, 95%, 96%, 97%, 98%, 99%, 99.5%, 99.9%, 99.99% or 100% of the relevant cytosine positions are the same for the presence of the DIMP, DIMR or DIGR of interest to be present in the sample methylome.

Plants, Characteristics and Epigenetic Modification

The present method is particularly useful in plants, where heritable DNA methylation differences in parental plants affect plant phenotypes and traits such as higher yields and stress tolerance. Parental plants include parents with heterotic combining ability and plants specifically altered in their DNA methylation patterns. One example of plants altered in their DNA methylation patterns are plants in which the plants or their progenitors have been suppressed for Msh1 expression. Such plants, or their progeny, when subsequently outcrossed and/or self-pollinated to restore Msh1 function, have been found to produce increase yields and/or acquire useful traits in the progeny through several methods [47]. These traits are heritable, non-genetic changes in plant phenotypes, depending on the crossing schemes used [48]. These plants contain new DNA methylation patterns [49].

For example, a reference plant (or wild-type plant) may be treated to suppress Msh1, to produce epigenetic variants of the plant. Msh1 function is then restored (for example, by outcrossing and/or self-pollinating), to produce the first of a new plant line. Further breeding to maintain this line or create new lines (such as by self-pollination, crossing and then self-pollination) may be used to produce F1, F2, F3, F4 and/or F5 progeny. The first of the new plant line may be crossed to an isogenic line (backcrossing) or an unrelated line (outcrossing) at any generation. Alternatively, the first of the new plant line may be selfed to produce S1, S2, S3, S4 and/or S5 or later generation progeny.

Examples of plants include those from the genera *Antirrhinum, Arabidopsis, Asparagus, Atropa, Avena, Beta, Brassica, Bromus, Browaalia, Capsicum, Chenopodium, Ciahorium, Citrus, Cucumis, Cucurbita, Datura, Daucus, Dendranthema, Digitalis, Fragaria, Geranium, Glycine, Gossypium, Helianthus, Heterocallis, Hordeum, Hyoscyamus, Juglans, Kalanchoe, Lactuca, Linum, Lolium, Lotus, Lycopersicon, Majorana, Malus, Manihot, Medicago, Nemesis, Nicotiana, Onobrychis, Oryza, Panieum, Pelargonium, Pennisetum, Petunia, Pharbitis, Phaseolus, Picea, Pinus, Pisum, Populus, Pseudotsuga, Ranunculus, Raphanus, Rosa, Salpiglossis, Secale, Senecio, Sinapis, Solanum, Trifolium, Trigonella, Triticale, Triticum, Vigna, Vitis,* and *Zea.*

Other examples of plants include corn (*Zea mays*), canola (*Brassica napus, Brassica rapa* ssp.), *Brassica* species useful as sources of seed oil, alfalfa (*Medicago sativa*), rice (*Oryza sativa*), rye (*Secale cereale*), sorghum (*Sorghum bicolor, Sorghum vulgare*), millet (for example, pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), duckweed (*Lemna*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucijra*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia* spp.), almond (*Prunus amygdalus*), sugar beets (*Beta vulgaris*), sugarcane (*Saccharum* spp.), oats, barley, vegetables, ornamentals, and conifers; vegetables plants, for example, tomatoes (*Lycopersicon esculentum*), lettuce (for example, *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*); ornamental plants, for example, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbiapulcherrima*), and *chrysanthemum*; leguminous plants, for example, guar, locust bean, fenugreek, soybean, garden beans, cowpea, mungbean, lima bean, fava bean, lentils, chickpea, peanuts (*Arachis* sp.), crown vetch (*Vicia* sp.), hairy vetch, adzuki bean, lupine (*Lupinus* sp.), *trifolium*, common bean (*Phaseolus* sp.), field bean (*Pisum* sp.), clover (*Melilotus* sp.) Lotus, trefoil, lens, and false indigo; forage and turf grass, for example, alfalfa (*Medicagos* sp.), orchard grass, tall fescue, perennial ryegrass, creeping bent grass, and redtop.

Examples of plant traits or characteristics include improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, and delayed senescence; agronomic traits (flowering time, days to flower, days to flower-post rainy, days to flowering; fungal disease resistance; grain related traits: (Grain dry weight, grain number, grain number per square meter, Grain weight over panicle, seed color, seed luster, seed size); growth and development stage related traits (basal tillers number, days to harvest, days to maturity, nodal tillering, plant height, plant height); inflorescence anatomy and morphology trait (threshability); Insect damage resistance; leaf related traits (leaf color, leaf midrib color, leaf vein color, flag leaf weight, leaf weight, rest of leaves weight); mineral and ion content related traits (shoot potassium content, shoot sodium content); panicle, pod, or ear related traits (number of panicles and seeds, harvest index, panicle weight); phytochemical compound content (plant pigmentation); xii) spikelet anatomy and morphology traits (glume color, glume covering); stem related trait (stem over leaf weight, stem weight); and miscellaneous traits (stover related traits, metabolised energy, nitrogen digestibility, organic matter digestibility, stover dry weight); various seed quality traits including improvements in either the compositions or amounts of oil, protein, or starch in the seed; increased biomass, non-flowering, male sterility, digestability, seed filling period, maturity (either earlier or later as desired), reduced lodging, and plant height (either increased or decreased as desired) improved resistance to biotic plant stress; stress imposed by plant fungal pathogens, plant bacterial pathogens, plant viral pathogens, insects, nematodes, and herbivores; resistance to fungal pathogens including, an *Alternaria* sp., an *Ascochyta* sp., a *Botrytis* sp.; a *Cercospora* sp., a *Colletotrichum* sp., a *Diaporthe* sp., a *Diplodia* sp., an *Erysiphe* sp., a *Fusarium* sp., *Gaeumanomyces* sp., *Helminthosporium* sp., *Macrophomina* sp., a *Nectria* sp., a *Peronospora* sp., a *Phakopsora* sp., *Phialophora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp, a *Pythium* sp., a *Rhizoctonia* sp., a *Scerotium* sp., a *Sclerotinia* sp., a *Septoria* sp., a *Thielaviopsis* sp., an *Uncinula* sp, a *Venturia* sp., and a *Verticillium* sp.; bacterial pathogens including *Erwinia* sp., a *Pseudomonas* sp., and a *Xanthamonas* sp.; resistance to insects including aphids and other piercing/sucking insects such as *Lygus* sp., lepidoteran insects such as *Armigera* sp., *Helicoverpa* sp., *Heliothis* sp., and *Pseudoplusia* sp., and coleopteran insects such as *Diabroticus* sp.; resistance to nematodes including *Meloidogyne* sp., *Heterodera* sp., *Belonolaimus* sp., *Ditylenchus* sp., *Globodera* sp., *Naccobbus* sp., and *Xiphinema* sp.

Other traits include yield improvements are improvements in the yield of a plant line relative to one or more parental line(s) under non-stress conditions. Non-stress conditions comprise conditions where water, temperature, nutrients, minerals, and light fall within typical ranges for cultivation of the plant species. Such typical ranges for cultivation comprise amounts or values of water, temperature, nutrients, minerals, and/or light that are neither insufficient nor excessive. In certain embodiments, such yield improvements are improvements in the yield of a plant line relative to parental line(s) under abiotic stress conditions. Such abiotic stress conditions include, but are not limited to, conditions where water, temperature, nutrients, minerals, and/or light that are either insufficient or excessive. Abiotic stress conditions would thus include, but are not limited to, drought stress, osmotic stress, nitrogen stress, phosphorous stress, mineral stress, heat stress, cold stress, and/or light stress. In this context, mineral stress includes, but is not limited to, stress due to insufficient or excessive potassium, calcium, magnesium, iron, manganese, copper, zinc, boron, aluminum, or silicon. In this context, mineral stress includes, but is not limited to, stress due to excessive amounts of heavy metals including, but not limited to, cadmium, copper, nickel, zinc, lead, and chromium.

EXAMPLES

Example 1: Identification of *Arabidopsis thaliana* with and without Enhanced Growth The concepts and heuristic described above were applied to distinguish the phenotypes of msh1 mutant, grafting Col0-msh1, and Epi-lines without and with enhance growth. This application leads to the detection of DIGRs mainly located in transposable elements (TEs) and transposable elements genes (TE genes). The strongest methylation signal induced by the msh1 is located in TEs and TEs genes. However, it does not mean the non-existence of DIGRs covering gene regions.

Most of the DIGRs detected in the analysis that were able to distinguish between Epi-lines without and with enhance growth were located in gene regions. The application of the heuristic (at step 5) produced results that indicated that these DIGRs are able to classify the whole set of samples mentioned above with very high classification accuracy. That is, the DIGRs that were able to distinguish between the phenotypes of Epi-lines without and with enhance growth can also be used to classify the whole set of samples with high classification accuracy.

The survey of the methylation profile at each DIGRs indicates that these GRs carry several DNA methylation patterns that are consistently present in all the Epi-lines with enhanced growth. For example, in FIG. 1, red lines correspond to the methylation profile of the Epi-lines with enhanced growth, while blue lines correspond to the Epi-lines without enhance growth and the wild-type methylation profiles. Red arrows indicate hypermethylation and blue arrows hypomethylation. 1A: Dicer-like 3 gene (DCL3, AT3G43920.1). 1B: LSD1-like2 gene (AT3G13682). 1C: ER to Golgi vesicle-mediated transport. COPII vesicle coat (AT3G44340.1). 1D: Teosinte branched 1, cycloidea. Belongs to a TCP protein transcription factor family (AT3G27010.1). 1E: Transcription factor IIIC, subunit 5 (AT3G49410.1). 1F: Riboflavin biosynthetic process (AT3G47390.1). In panels 1A and 1D to 1F, the Epi-lines with enhance growth are hypermethylated in respect to the wildtypes and Epi-lines without enhanced growth; while the reverse situation is shown in panel 1B and 1C.

Example 2: EpiQTL Detection

The overlap between DIGRs and differentially expressed genes (DEGs) from Epi-lines samples yields 351 DEGs. Examples of some of DIGRs-DEGs detected are presented in Table 2. Genes linked to stress resistance, plant development, auxin and brassinosteroid signalling pathways are between 351 DIGRs-DEGs detected.

TABLE 2

Differentially expressed genes from epi-lines overlapping at least in 20 bp with the DIGRs in Epi-lines (Gene IDs in red are upregulated, otherwise downregulated).

| Locus | Full list of Gene ontology described for the locus |
|---|---|
| AT1G08465.1 | GO: 0010158 abaxial cell fate specification\|GO: 0003700 transcription factor activity, sequence-specific DNA binding\|GO: 0005634 nucleus |

TABLE 2-continued

Differentially expressed genes from epi-lines overlapping at least in 20 bp with the DIGRs in Epi-lines (Gene IDs in red are upregulated, otherwise downregulated).

| Locus | Full list of Gene ontology described for the locus |
|---|---|
| AT1G08810.1 | GO: 0006355 regulation of transcription, DNA-templated\|GO: 0009414 response to water deprivation\|GO: 0009416 response to light stimulus\| GO: 0009737 response to abscisic acid\|GO: 0009751 response to salicylic acid\| GO: 0009753 response to jasmonic acid\|GO: 0010118 stomatal movement\| GO: 0003677 DNA binding\|GO: 0003700 transcription factor activity, sequence-specific DNA binding\|GO: 0005634 nucleus |
| AT1G08810.2 | GO: 0006355 regulation of transcription, DNA-templated\|GO: 0009414 response to water deprivation\|GO: 0009416 response to light stimulus\| GO: 0009737 response to abscisic acid\|GO: 0009751 response to salicylic acid\| GO: 0009753 response to jasmonic acid\|GO: 0010118 stomatal movement\| GO: 0003677 DNA binding\|GO: 0003700 transcription factor activity, sequence-specific DNA binding\|GO: 0005634 nucleus |
| AT4G02560.1 | GO: 0009911 positive regulation of flower development\|GO: 0010228 vegetative to reproductive phase transition of meristem\|GO: 0003700 transcription factor activity, sequence-specific DNA binding\|GO: 0005515 protein binding\|GO: 0005634 nucleus |
| AT1G20050.1 | GO: 0006084 acetyl-CoA metabolic process\|GO: 0016126 sterol biosynthetic process\|GO: 0016132 brassinosteroid biosynthetic process\|GO: 0019932 second-messenger-mediated signaling\|GO: 0060964 regulation of gene silencing by miRNA\|GO: 0000247 C-8 sterol isomerase activity\|GO: 0005886 plasma membrane |
| AT5G02460.1 | GO: 0006355 regulation of transcription, DNA-templated\|GO: 0003677 DNA binding\|GO: 0003700 transcription factor activity, sequence-specific DNA binding\|GO: 0005634 nucleus |
| AT5G65080.1 | GO: 0009910 negative regulation of flower development\|GO: 0010048 vernalization response\|GO: 0043481 anthocyanin accumulation in tissues in response to UV light\|GO: 0048440 carpel development\|GO: 0048587 regulation of short-day photoperiodism, flowering\|GO: 2000028 regulation of photoperiodism, flowering\|GO: 0003700 transcription factor activity, sequence-specific DNA binding\|GO: 0005634 nucleus |
| AT1G04250.1 | GO: 0009733 response to auxin\|GO: 0009734 auxin-activated signaling pathway\|GO: 0003700 transcription factor activity, sequence-specific DNA binding\|GO: 0005515 protein binding\|GO: 0042802 identical protein binding\| GO: 0000502 proteasome complex\|GO: 0005634 nucleus\|GO: 0008180 COP9 signalosome\|GO: 0019005 SCF ubiquitin ligase complex |
| AT4G12980.1 | (Auxin-responsive family protein)\|GO: 0007275 multicellular organismal development\|GO: 0009507 chloroplast\|GO: 0016020 membrane |
| AT5G65080.2 | GO: 0009910 negative regulation of flower development\|GO: 0010048 vernalization response\|GO: 0043481 anthocyanin accumulation in tissues in response to UV light\|GO: 0048587 carpel development\|GO: 0048587 regulation of short-day photoperiodism, flowering\|GO: 2000028 regulation of photoperiodism, flowering\|GO: 0003700 transcription factor activity, sequence-specific DNA binding\|GO: 0005634 nucleus |

The gene ontologies (GOs) found in the set of 351 DIGRs-DEGs was also detected in an alternative way. In this case, the subset of genes with differentially expressed exons (DEEs) linked to alternative splicing and carrying DIMPs in the region covering the DEEs-splice-junction was analyzed for gene enrichment. The R package EnrichmentBrowser was used to perform Gene Graph Enrichment Analysis (GGEA), which is a network-based enrichment analysis method [61,62]. Some of the regulatory networks detected in Epi-lines are shown in FIG. 3.

Figure 4:
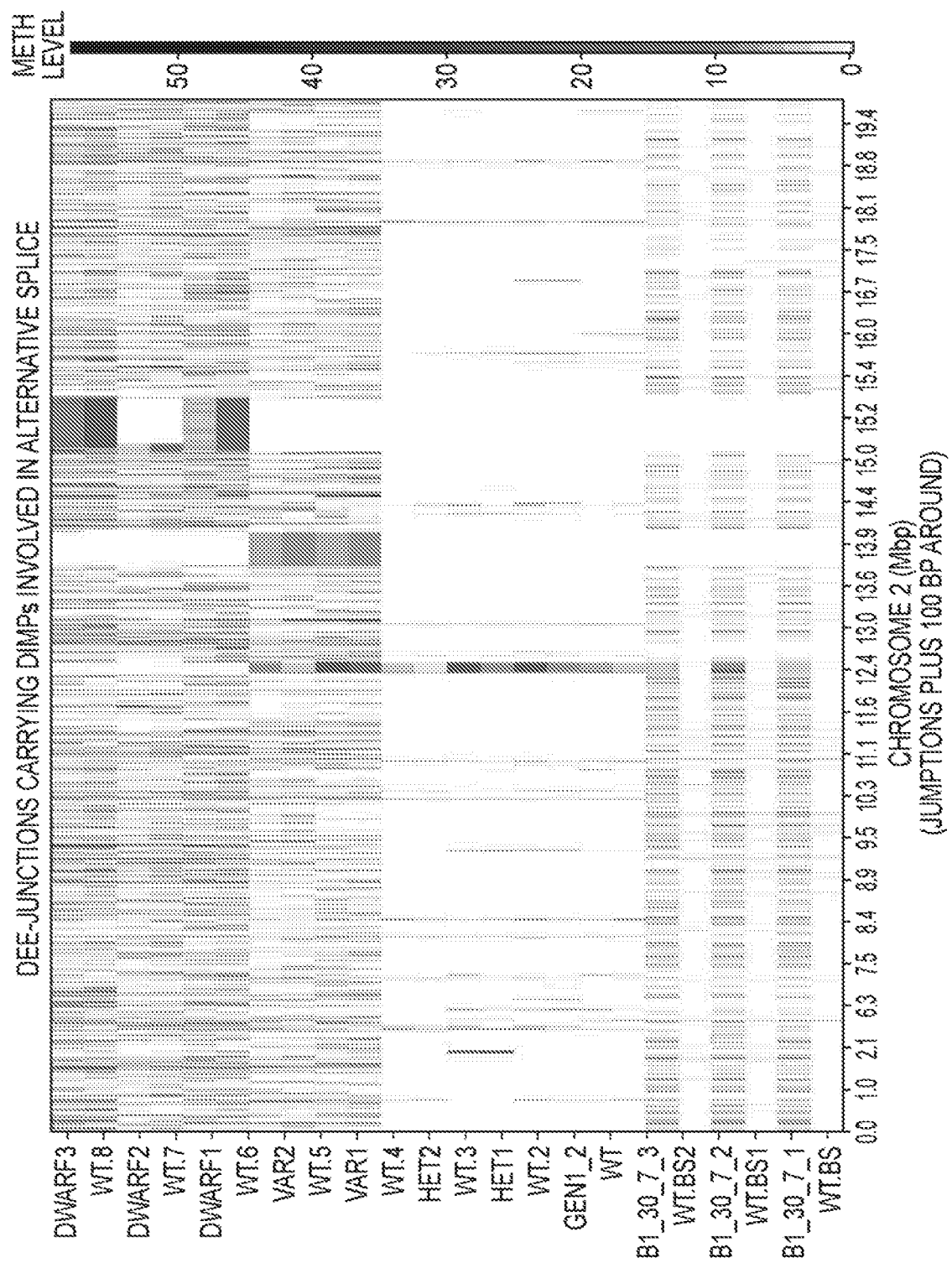
FIG. 4 and FIG. 5 are heat-maps (a graph of genomic position verses the presence of DIGRs, each for a different methylomes) from chromosome 2 and 3 at the gene regions DEEs-splice-junction carrying DIMPs. The samples involved are: first generation wildtype segregant from a heterozygote parent (Wt), first generation heterozygote (het), second generation msh1 TDNA mutants, variegated (var) and dwarf plants.

All the regulatory networks detected by the application of GGEA in genes with DEEs-splice-junction carrying DIMPs in samples from second generation of msh1 TDNA mutants: variegates and dwarf plants, and Epi-lines plants are presented in Table 3. The Venn diagram with the intersection of these networks in these samples is shown in FIG. 4.

Figure 3:
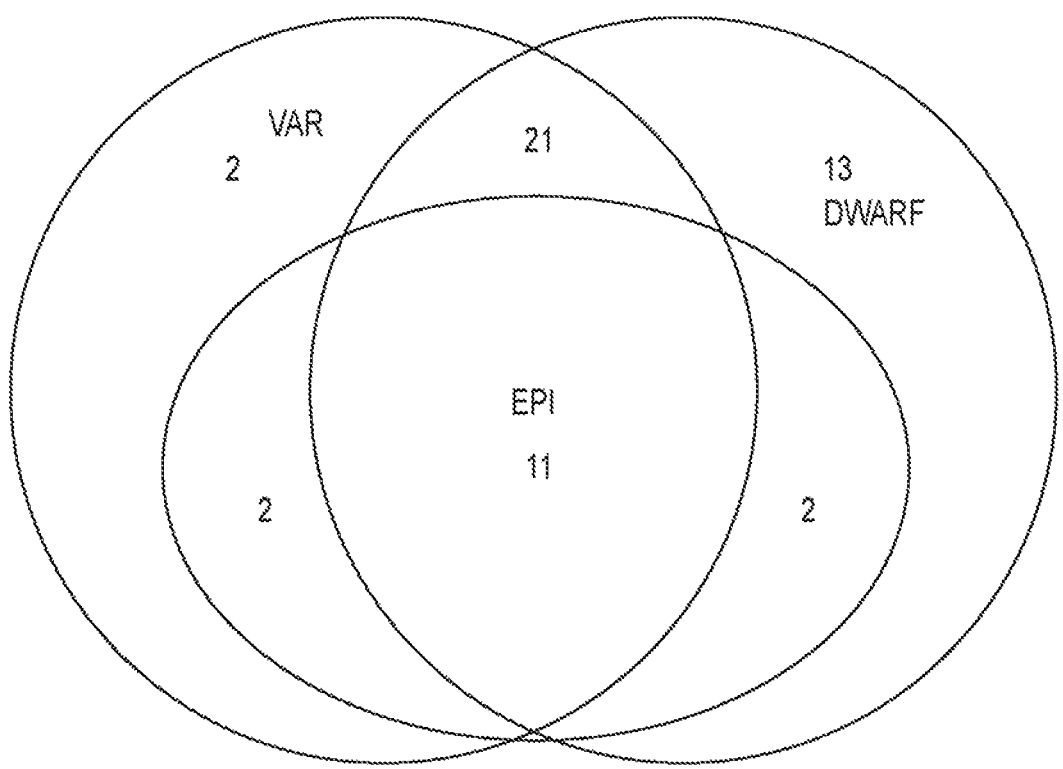
FIG. 3 is a Venn diagram showing the intersection of the statistical different network regulatory pathways detected by the application of Gene Graph Enrichment Analysis (GGEA) to the samples: second generation of msh1 TDNA mutants, *variegates* and dwarf plants, and Epi-lines plants. The integers in the diagram indicate the number of regulatory networks detected that integrate each subset.
Figure 5:
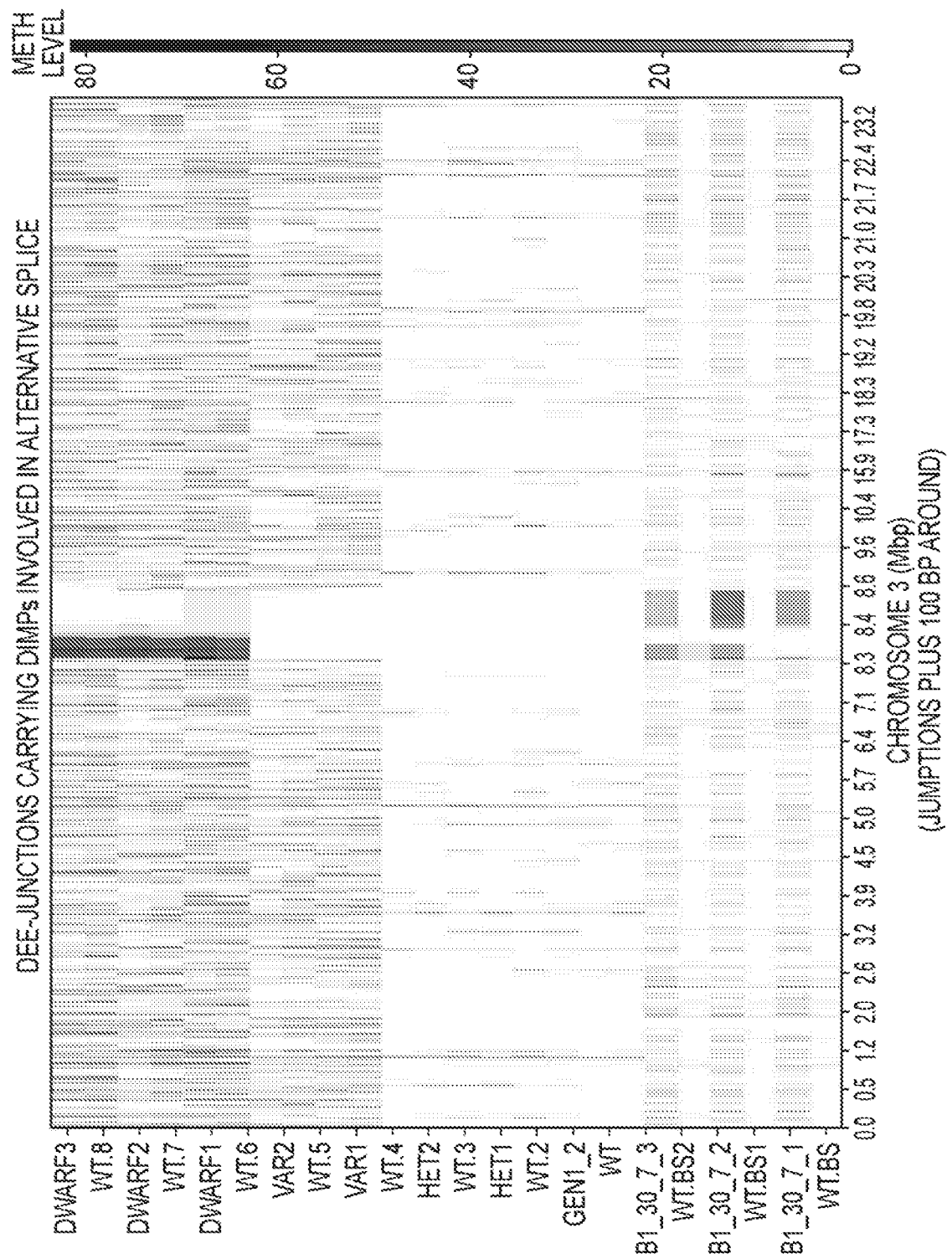

Results so far indicate that gene regions covering DEEs-splicing-junctions carrying DIMPs are linked to key regulatory genes controlling the regulatory networks (FIG. 3, Table 3). Heat-maps of the subset of gene regions of DEEs-junctions carrying DIMPs indicate that significant methylation changes takes place in those regions. In particular, these heat-maps suggest the existence of genome-wide methylation hotspots around DEEs-junctions regions (FIG. 5).

| Dwarf |
|---|
| GO: 0006355_regulation_of_transcription,_DNA-templated |
| GO: 0007623_circadian_rhythm |
| GO: 0009617_response_to_bacterium |
| GO: 0009639_response_to_red_or_far_red_light |
| GO: 0009733_response_to_auxin |
| GO: 0009862_systemic_acquired_resistance,_salicylic_acid_mediated_signaling_pathway |
| GO: 0009867_jasmonic_acid_mediated_signaling_pathway |
| GO: 0042742_defense_response_to_bacterium |

GO: 0042752__regulation__of__circadian__rhythm
GO: 0048574__long-day__photoperiodism,__flowering
GO: 0050832__defense__response__to__fungus
GO: 0000165__MAPK__cascade
GO: 0016301__kinase__activity
GO: 0003700__transcription__factor__activity,__sequence-specific__DNA__binding
GO: 0007154__cell__communication
GO: 0009409__response__to__cold
GO: 0009414__response__to__water__deprivation
GO: 0009595__detection__of__biotic__stimulus
GO: 0006612__protein__targeting__to__membrane
GO: 0009627__systemic__acquired__resistance
GO: 0009651__response__to__salt__stress
GO: 0009697__salicylic__acid__biosynthetic__process
GO: 0009737__response__to__abscisic__acid
GO: 0009814__defense__response,__incompatible__interaction
GO: 0009863__salicylic__acid__mediated__signaling__pathway
GO: 0010200__response__to__chitin
GO: 0010310__regulation__of__hydrogen__peroxide__metabolic__process
GO: 0010363__regulation__of__plant-type__hypersensitive__response
GO: 0031348__negative__regulation__of__defense__response
GO: 0031537__regulation__of__anthocyanin__metabolic__process
GO: 0034976__response__to__endoplasmic__reticulum__stress
GO: 0042538__hyperosmotic__salinity__response
GO: 0043069__negative__regulation__of__programmed__cell__death
GO: 0043900__regulation__of__multi-organism__process
GO: 0003677__DNA__binding
GO: 0005783__endoplasmic__reticulum
GO: 0006970__response__to__osmotic__stress
GO: 0009611__response__to__wounding
GO: 0009723__response__to__ethylene
GO: 0009736__cytokinin-activated__signaling__pathway
GO: 0009738__abscisic__acid-activated__signaling__pathway
GO: 0009753__response__to__jasmonic__acid
GO: 0010029__regulation__of__seed__germination
GO: 0030968__endoplasmic__reticulum__unfolded__protein__response
GO: 0035556__intracellular__signal__transduction
GO: 0043424__protein__histidine__kinase__binding
GO: 0048831__regulation__of__shoot__system__development
Variegated GO: 0006355__regulation__of__transcription,__DNA-templated
GO: 0007623__circadian__rhythm
GO: 0009410__response__to__xenobiotic__stimulus
GO: 0009617__response__to__bacterium
GO: 0009639__response__to__red__or__far__red__light
GO: 0009733__response__to__auxin
GO: 0009742__brassinosteroid__mediated__signaling__pathway
GO: 0009862__systemic__acquired__resistance,__salicylic__acid__mediated__signaling__pathway
GO: 0009867__jasmonic__acid__mediated__signaling__pathway
GO: 0042742__defense__response__to__bacterium
GO: 0042752__regulation__of__circadian__rhythm
GO: 0048574__long-day__photoperiodism,__flowering
GO: 0050832__defense__response__to__fungus
GO: 0000165__MAPK__cascade
GO: 0007154__cell__communication
GO: 0009409__response__to__cold
GO: 0009414__response__to__water__deprivation
GO: 0009595__detection__of__biotic__stimulus
GO: 0006612__protein__targeting__to__membrane
GO: 0009627__systemic__acquired__resistance
GO: 0009651__response__to__salt__stress
GO: 0009697__salicylic__acid__biosynthetic__process
GO: 0009737__response__to__abscisic__acid
GO: 0009814__defense__response,__incompatible__interaction
GO: 0009863__salicylic__acid__mediated__signaling__pathway
GO: 0010200__response__to__chitin
GO: 0010310__regulation__of__hydrogen__peroxide__metabolic__process
GO: 0010363__regulation__of__plant-type__hypersensitive__response
GO: 0031348__negative__regulation__of__defense__response
GO: 0031537__regulation__of__anthocyanin__metabolic__process
GO: 0034976__response__to__endoplasmic__reticulum__stress
GO: 0042538__hyperosmotic__salinity__response -continued GO: 0043069_negative_regulation_of_programmed_cell_death
GO: 0043900_regulation_of_multi-organism_process
GO: 0000156_phosphorelay_response_regulator_activity
GO: 0009735_response_to_cytokinin Epi-line GO: 0006355_regulation_of_transcription,_DNA-templated
GO: 0007623_circadian_rhythm
GO: 0009410_response_to_xenobiotic_stimulus
GO: 0009617_response_to_bacterium
GO: 0009639_response_to_red_or_far_red_light
GO: 0009733_response_to_auxin
GO: 0009742_brassinosteroid_mediated_signaling_pathway
GO: 0009862_systemic_acquired_resistance,_salicylic_acid_mediated_signaling_pathway
GO: 0009867_jasmonic_acid_mediated_signaling_pathway
GO: 0042742_defense_response_to_bacterium
GO: 0042752_regulation_of_circadian_rhythm
GO: 0048574_long-day_photoperiodism,_flowering
GO: 0050832_defense_response_to_fungus
GO: 0016301_kinase_activity
GO: 0003700_transcription_factor_activity,_sequence-specific_DNA_binding

Example 3: (Prophetic) Identification of *Arabidopsis thaliana* with and without Enhance Growth Plants from Epi-lines without and with enhance growth are randomly planted. A leaf sample is collected from each plant and placed in a labeled container which identified which plant it was taken from. Methylome data for each sample is prepared using DNA isolation and DNA bisulfite conversion methodology coupled with next-generation sequencing approaches (Bis-seq). Each methylome collected is associated with a specific plant. The methylome data for each plant is examined for the DIGRs identified in Example 1. All plants having a methylome containing the DIGRs for enhance growth are retained, while the remaining plants are destroyed. The result is a collection of plants, most of which when mature will display the phenotypic characteristic of enhanced growth.

Example 4. Identification of Plants with and without Enhanced Growth

The methods of Example 3 are followed except that leaf tissue is isolated from the specific plant of interest, such as crop plants including corn, soybeans, wheat, rice, sorghum, potatoes, and tomatoes. DIGRs are prepared for each species by the methods described herein, where the sample plants have high yields and the reference plant or plants do not.

Example 5. Maize Tissue DNA Isolation from Embryo Scutellum Tissue

A small piece of the scutellum of the embryo of a maize seed is isolated by cutting the edge of the scutellum of a seed with a scalpel to remove a small portion of scutellum tissue for DNA isolation and analysis. The embryo axis is not damaged in removing this fragment of scutellum and the seed can germinate normally. DNA from the isolated scutellum fragment is isolated tissue using the DNeasy Plant Mini Kit according to the manufacturer's protocol (Qiagen, Valencia, Calif.), and DNA content is quantified by Qubit HS dsDNA kit.

This protocol is also suitable for isolating DNA from cotyledons, seedling leaf tissue, pollen, immature tassels, and/or immature ears, also provide DNA suitable for methylation analysis, and may be applied to other plant species described in the present application. To reduce splitting when isolating scutellum or cotyledon fragments, seed should be humidified to moisture level of 12%. When pretreated in this manner, splitting is significantly reduced. DNA from the isolated scutellum fragment is isolated tissue using the DNeasy Plant Mini Kit according to the manufacturer's protocol (Qiagen, Valencia, Calif.), and DNA content is quantified by Qubit HS dsDNA kit.

Example 6. Bisulfite Treatment of Isolated DNA, Sequencing and Data Collection Approximately 500 ng gDNA is double digested using SacI (GAGCTC) and MseI (TTAA) (Fermentas) in a reaction volume of 25 μl. The reaction mixture is first incubated at 37° C. for 6 hours, and then at 65° C. for 90 minutes. Methylated SacI and MseI adaptors are annealed using the following annealing program: 94° C. gradually decreased to 65° C. with −0.5° C. every 10 seconds, then kept at 65° C. for 10 minutes, 56° C. for 10 minutes, 37° C. for 10 minutes, and 22° C. for 10 minutes. Restriction fragments are ligated to methylated SacI and MseI adaptors. The ligation reaction is carried out in 50 μl at 16° C. overnight with 25 pmol methylated SacI and MseI adaptors, and 50,000 Units of T4 DNA ligase (NEB). The resulting ligated DNA is concentrated using a PCR purification kit (Qiagen, Valencia, Calif.) and fragments between 250 and 500 bp are cut from a 2% agarose gel and purified with a Qiagen gel purification kit (Qiagen, Valencia, Calif.). About 500 ng recovered products are subjected to two successive treatments with sodium bisulfite using EpiTect Bisulfite kit (Qiagen, Valencia, Calif.) following the manufacturer's instructions. After a final purification using the PCR purification kit, 5 μl bisulfite-converted ligates are amplified by 18 PCR cycles with the following reaction composition: 1×Taq buffer, 3.5 mM MgCl$_2$, 0.4 mM dNTPs, 1 U Taq DNA polymerase (Fermentas), and 5 pmol Illumina PCR primers. The enriched library is purified with a Qiagen gel purification kit, and quantified by Qubit HS dsDNA kit. The library is sequenced on a Hiseq 2000 platform according to the manufacturer's instructions. The first 75 bp of paired-end (PE) reads are retained, and the residual enzyme recognition sequences trimmed. Low-quality PE reads containing more than 5% of nucleotides with Phred quality value<30 are filtered by the IlluQC.pl script included in NGSQCToolkit_v2.3 program. The remaining high-quality reads are mapped against the reference genome et sequence using Bismark_v0.7.4 software in a non-directional manner with a maximum of 1 bp mismatch in multi-seed alignment. Only uniquely mapped reads are retained for further analyses.

Appendix: Derivation of the Generalized Gamma Distribution

The derivation of the Generalized Gamma Distribution follow the derivation given by Lienhard in reference [65], just that the premises/assumptions are rewritten in the context of cytosine DNA methylation (CDM).

A methylation change at a genomic region R has an associated amount of information $I_R$ processed by the activity of methyltransferases and demethylases. To estimate the amount of information associated with methylation changes, a methylome is split to N genomic regions of length l, and information $I_R$ is computed according to Eq. 3 in each region R. Under Landauer's principle, the minimum energy dissipated to process the information $I_R$ can be approached by equation Eq. 4.

Let $N_i$ be the number of time that an amount of energy with values in the interval $\lfloor E_R^{i-1} E_R^i)$ was dissipated in N genomic regions (GRs). The following requirements are imposed upon $N_i$:

The total number of occurrence of the event is fixed: $\Sigma_i N_i = N$ $N_i$'s and N are assumed large numbers.

For each choice of ε the following sum is positive constant:

$$\sum_i \frac{N_i}{N}(E_R^i)^\delta = K$$

The number of distinguishable ways, $n_i$, in which the event can occur with values in the interval $\lfloor E_R^{i-1} E_R^i)$ is proportional to a specific power of $E_R^i$. That is, $n_i = A(E_R^i)^{v-1}$;

In addition, δ, v, and K>0. Now, the derivation of the probability density function (CDF) $f(E_R)$ follows as is described by Lienhard and Meyer in reference [1], which yield a generalized gamma distribution (GG) with the parametrization given by Stacy in reference [66]:

$$f(E_R \mid a, \delta, v) = \frac{\delta}{a^v \Gamma(v/\delta)} E_R^{v-1} e^{-\left(\frac{E_R}{a}\right)^\delta}$$

The form commonly used in practice is obtained by the parametrization: $\psi=v/\delta$, $\beta=a$, and $\alpha=\delta$:

$$f(E_R \mid a, \beta, \psi) = \frac{\delta}{\beta \Gamma(\psi)} \left(\frac{E_R}{\beta}\right)^{\alpha\psi-1} e^{-\left(\frac{E_R}{\beta}\right)^\alpha}$$

After splitting a methylome into relatively large genomic regions, it is possible that every region carries at least one or more methylation changes in such a way that $E_R \geq \eta > 0$ for all regions R. From a statistical point of view η is a location parameter and, in this case, the last equation adopts the form:

$$f(E_R \mid \alpha, \beta, \eta, \psi) = \frac{\alpha}{\beta \Gamma(\psi)} \left(\frac{E_R-\eta}{\beta}\right)^{\alpha\psi-1} e^{-\left(\frac{E_R-\eta}{\beta}\right)^\alpha}, \; E_R > \eta > 0$$

Since methylation changes can take place with random fluctuations in thermal noise, the scaling parameter β(l) can be set equal to the average energy per DNA molecule in thermal equilibrium. That is, $\beta(l)=\varphi(l)k_B T$ (12), where $\varphi(l)$ expresses the contribution of all degrees of freedom to the average energy per molecule as a function of genomic region length l.

REFERENCES

1. Law J, Jacobsen S E (2010) Establishing, maintaining and modifying DNA methylation patterns in plants and animals. Nat Rev Genet 11: 204-220. Available: www.pubmedcentral.nih.gov/articlerender.fcgi?artid=3034103&tool=pmcentrez&rendert ype=abstract.
2. Ramchandani S, Bhattacharya S K, Cervoni N, Szyf M (1999) DNA methylation is a reversible biological signal. Proc Natl Acad Sci USA 96: 6107-6112. Available: www.pubmedcentral.nih.gov/articlerender.fcgi?artid=26843&ttoo=pmcentrez&rendertyp e=abstract.
3. Schneider T D (1991) Theory of molecular machines. II. Energy dissipation from molecular machines. J Theor Biol 148: 125-137. Available: www.ncbi.nlm.nih.gov/pubmed/2016881.
4. Bérut A, Arakelyan A, Petrosyan A, Ciliberto S, Dillenschneider R, et al. (2012) Experimental verification of Landauer's principle linking information and thermodynamics. Nature 483: 187-189. Available: www.ncbi.nlm.nih.gov/pubmed/22398556.
5. Esteller M (2008) Epigenetics in cancer. N Engl J Med 358: 1148-1159. Available: www.ncbi.nlm.nih.gov/pubmed/18337604.
6. Shannon C. E (1948) A Mathematical Theory of Communication. Bell Syst Tech J 27: 379-423.
7. Jaynes E T (1957) Information Theory and Statistical Mechanics. Phys Rev 106: 620-630. Available: link.aps.org/doi/10.1103/PhysRev. 106.620.
8. Toyabe S, Sagawa T, Ueda M, Muneyuki E, Sano M (2010) Experimental demonstration of information-to-energy conversion and validation of the generalized Jarzynski equality. Nat Phys 6: 988-992. Available: www.nature.com/doifinder/10.1038/nphys1821.
9. Xie H, Wang M, de Andrade A, Bonaldo M D F, Galat V, et al. (2011) Genome-wide quantitative assessment of variation in DNA methylation patterns. Nucleic Acids Res 39: 4099-4108. Available: www.pubmedcentral.nih.gov/articlerender.fcgi?artid=3105398&tool=pmcentrez&rendert ype=abstract.
10. Mercadante D, Melton L D, Jameson G B, Williams M a K (2014) Processive pectin methylesterases: the role of electrostatic potential, breathing motions and bond cleavage in the rectification of Brownian motions. PLoS One 9: e87581. Available: www.pubmedcentral.nih.gov/articlerender.fcgi?artid=3913658&tool=pmcentrez&rendert ype=abstract.
11. Koslover E F, Spakowitz A J (2012) Force fluctuations impact kinetics of biomolecular systems. Phys Rev E Stat Nonlin Soft Matter Phys 86: 011906. Available: www.ncbi.nlm.nih.gov/pubmed/23005451.
12. Severin P M D, Zou X, Gaub H E, Schulten K (2011) Cytosine methylation alters DNA mechanical properties. Nucleic Acids Res 39: 8740-8751. Available: www.pubmedcentral.nih.gov/articlerender.fcgi?artid=3203585&tool=mcentrez&rendert ype=abstract.

13. Phelps C, Lee W, Jose D, von Hippel P H, Marcus A H (2013) Single-molecule FRET and linear dichroism studies of DNA breathing and helicase binding at replication fork junctions. Proc Natl Acad Sci USA 110: 17320-17325. Available: www.pubmedcentral.nih.gov/articlerender.fcgi?artid=3808625&tool=pmcentrez&rendert ype=abstract.
14. Rubin A, Riznichenko G (2014) Nonlinear Models of DNA Dynamics DNA dynamics. Mathematical Biophysics SE-8. Biological and Medical Physics, Biomedical Engineering. Springer US. pp. 117-138. Available: dx.doi.org/10.1007/978-1-4614-8702-9_8.
15. Schmitz R J R, Schultz M D M, Lewsey M M G, O'Malley R C, Urich M a, et al. (2011) Transgenerational epigenetic instability is a source of novel methylation variants. Science (80) 334: 369-373. Available: www.sciencemag.org/content/334/6054/369.short.
16. Havecker E R, Wallbridge L M, Fedito P, Hardcastle T J, Baulcombe D C (2012) Metastable differentially methylated regions within *Arabidopsis* inbred populations are associated with modified expression of non-coding transcripts. PLoS One 7: e45242. Available: www.pubmedcentral.nih.gov/articlerender.fcgi?artid=3447930&tool=pmcentrez&rendert ype=abstract.
17. Armond J W, Saha K, Rana A a, Oates C J, Jaenisch R, et al. (2014) A stochastic model dissects cell states in biological transition processes. Sci Rep 4: 3692. Available: www.pubmedcentral.nih.gov/articlerender.fcgi?artid=3894565&tool=pmcentrez&rendert ype=abstract.
18. Adami C (2004) Information theory in molecular biology. Phys Life Rev 1: 3-22. Available: linkinghub.elsevier.com/retrieve/pii/S157106450400003X.
19. Tribus M, McIrvine E C (1971) Energy and Information. Sci Am 225: 179-188. doi:doi:10.1038/scientificamerican0971-179.
20. Dillenschneider R, Lutz E (2009) Memory Erasure in Small Systems. Phys Rev Lett 102: 210601. Available: link.aps.org/doi/10.1103/PhysRevLett. 102.210601.
21. Liu Y, Bahar 1 (2012) Sequence evolution correlates with structural dynamics. Mol Biol Evol 29: 2253-2263. Available: www.pubmedcentral.nih.gov/articlerender.fcgi?artid=3424413&tool=pmcentrez&rendert ype=abstract.
22. Schneider T D (1994) Sequence logos, machine/channel capacity, Maxwell's demon, and molecular computers: a review of the theory of molecular machines. Nanotechnology 5: 1-18. doi:doi:10.1088/0957-4484/5/1/001.
23. Oyeyemi O a, Sours K M, Lee T, Resing K a, Ahn N G, et al. (2010) Temperature dependence of protein motions in a thermophilic dihydrofolate reductase and its relationship to catalytic efficiency. Proc Natl Acad Sci USA 107: 10074-10079. Available: www.pubmedcentral.nih.gov/articlerender.fcgi?artid=2890430&tool=mcentrez&rendert ype=abstract.
24. Klinman J P, Kohen A (2013) Hydrogen tunneling links protein dynamics to enzyme catalysis. Annu Rev Biochem 82: 471-496. Available: www.pubmedcentral.nih.gov/articlerender.fcgi?artid=4066974&tool=pmcentrez&rendert ype=abstract.
25. Klinman J P (2010) An integrated model for enzyme catalysis emerges from studies of hydrogen tunneling. Chem Phys Lett 471: 179-193. doi:10.1016/j.cplett.2009.01.038.An.
26. Schneider T D (2010) 70% efficiency of bistate molecular machines explained by information theory, high dimensional geometry and evolutionary convergence. Nucleic Acids Res 38: 5995-6006. Available: dx.doi.org/10.1093/nar/gkq389.
27. Benjamini Y (2010) Discovering the false discovery rate. J R Stat Soc Ser B (Statistical Methodol 72: 405-416. Available: dx.doi.org/10.1111/j.1467-9868.2010.00746.x.
28. Becker C, Hagmann J, Müller J, Koenig D, Stegle O, et al. (2011) Spontaneous epigenetic variation in the *Arabidopsis thaliana* methylome. Nature 480: 245-249. Available: www.ncbi.nlm.nih.gov/pubmed/22057020.
29. Schmitz R J, Schultz M D, Urich M a, Nery J R, Pelizzola M, et al. (2013) Patterns of population epigenomic diversity. Nature 495: 193-198. Available: www.ncbi.nlm.nih.gov/pubmed/23467092.
30. Dawy Z, Hanus P, Weindl J, Dingel J, Morcos F (2007) On genomic coding theory. Eur Trans Telecommun 18: 873-879. Available: dx.doi.org/10.1002/ett. 1201.
31. Lorenzo-Ginori J V, Rodriguez-Fuentes A, Abalo R G, Sanchez R (2009) Digital Signal Processing in the Analysis of Genomic Sequences. Curr Bioinform 4: 28-40. Available: www.ingentaconnect.com/content/ben/cbio/2009/00000004/00000001/art00004.
32. R Core Team (2014) A language and environment for statistical computing. Available: www.r-project.org/.
33. Lawrence M, Huber W, Pages H, Aboyoun P, Carlson M, et al. (2013) Software for computing and annotating genomic ranges. PLoS Comput Biol 9: e1003118. Available: www.pubmedcentral.nih.gov/articlerender.fcgi?artid=3738458&tool=pmcentrez&rendert ype=abstract.
34. Xi Y, Li W (2009) BSMAP: whole genome bisulfite sequence MAPping program. BMC Bioinformatics 10: 232. Available: www.pubmedcentral.nih.gov/articlerender.fcgi?artid=2724425&tool=pmcentrez&rendert ype=abstract.
35. Lawrence M, Gentleman R, Carey V (2009) rtracklayer: an R package for interfacing with genome browsers Michael. Bioinformatics 25: 1841-1842. Available: www.pubmedcentral.nih.gov/articlerender.fcgi?artid=2705236&ttoo=pmcentrez&rendert ype=abstract.
36. Stevens J P (2009) Applied Multivariate Statistics for the Social Sciences. Fifth Edit. Routledge Academic. p. 664.
37. Hall M, Frank E, Holmes G, Pfahringer B, Reutemann P, et al. (2009) The WEKA Data Mining Software: An Update. SIGKDD Explor 11.
38. Josse J (2008) FactoMineR: An R Package for Multivariate Analysis. J Stat Softw 25: 1-18.
39. Ma, B. et al. (2014) Predicting DNA methylation level across human tissues. Nucleic Acids Research, 2014, 1-14. doi:10.1093/nar/gktl380.
40. Backlin, C. (2015) Machine Learning Based Analysis of DNA Methylation Patterns in Pediatric Acute Leukemia. Digital Comprehensive Summaries of Uppsala Dissertations from the Faculty of Medicine 1069. Available: uu.diva-portal.org/smash/get/diva2:784373/FULLTEXT01.pdf
41. Jombart, T. (2008) adegenet: a R package for the multivariate analysis of genetic markers. Bioinformatics 24: 1403-1405.
42. Available at www.cs.waikato.ac.nz/ml/weka/
43. Kass G V. (1980) An Exploratory Technique for Investigating Large Quantities of Categorical Data. Appl Stat 29: 119. doi:10.2307/2986296
44. U.S. Pat. App., Pub. No. US 2012/0284814

45. Kumar et al. 2013 J Genet 92(3): 629-666
46. Cortijo et al. 2014 Science. 2014 Mar. 7; 343(6175): 1145-8
47. U.S. Pat. App., Pub. Nos. US 2015/0189842, US 2015/0052630, US 2015/0113679 and US 2012/0284814.
48. Yang X, Kundariya H, Xu Y Z, Sandhu A, Yu J, Hutton S F, Zhang M, Mackenzie S A. Plant Physiol. 2015 May; 168(1):222-32; de la Rosa Santamaria R, Shao M R, Wang G, Nino-Liu D O, Kundariya H, Wamboldt Y, Dweikat I, Mackenzie S A. PLoS One. 2014 Oct. 27; 9(10):e108407
49. Virdi K S, Laurie J D, Xu Y Z, Yu J, Shao M R, Sanchez R, Kundariya H, Wang D, Riethoven J J, Wamboldt Y, Arrieta-Montiel M P, Shedge V, Mackenzie S A. Nat Commun. 2015 Feb. 27; 6:6386
50. See, for example, Rabinowicz, et al. Genome Res. 13: 2658-2664 2003; Li et al., Plant Cell 20:259-276, 2008; Frommer et al. Proc. Natl. Acad. Sci. U.S.A. 89 (5): 1827-31; Tost et al. BioTechniques 35 (1): 152-156, 2003; Herman et al. Proc. Natl. Acad. Sci. U.S.A. 93 (18): 9821-6, 1996; Wang et al. The Plant Cell 21:1053-1069 (2009); Wojdacz and Dobrovic (2007) Nucleic Acids Res. 35 (6): e41; Umezu et al. Anal Biochem. 415(2):145-50, 2011; Flusberg et al. Nature Methods 7, 461-465; MsSnuPE; and Gonzalgo and Jones Nucleic Acids Res. 25 (12): 2529-2531, 1997;
51. See, for example, U.S. Pat. Nos. 6,265,171; 7,037,650; 7,229,759; 7,820,385; 7,943,308; 7,972,784; 8,241,855; 8,273,528; 8,323,890; 8,361,719; 8,394,585; 8,440,404; and 8,586,302.
52. Chinnusamy V et al. Sci China Ser C-Life Sci. (2009) 52(4): 331-343.
53. See, for example, Franco-Zorilla et al. Plant J. 2009 59(5):840-50; Wang et al. The Plant Cell 21:1053-1069 (2009); Wei et al., Proc Natl Acad Sci USA. 2014 Feb. 19, 111(10): 3877-3882; Zhai et al., Methods. 2013 Jun. 28. pii: S1046-2023(13)00237-5. doi: 10.1016/j.ymeth.2013.06.025; J. Zhai et al., Methods (2013), dx.doi.org/10.1016/j.ymeth.2013.06.025; Rosas-Cardenas et al., (2011) Plant Methods 2011, 7:4; Moyano et al., BMC Genomics. 2013 Oct. 11; 14:701; Eldem et al., PLoS One. 2012; 7(12):e50298; Barber et al., Proc Natl Acad Sci USA. 2012 Jun. 26; 109(26):10444-9; and Gommans et al., Methods Mol Biol. 2012; 786:167-78.
54. See, for example, U.S. Pat. Nos. 7,550,583; 8,399,221; 8,399,222; 8,404,439; and 8,637,276.
55a. Stacy E W (1962) A Generalization of the Gamma Distribution. Ann Math Stat 33: 1187-1192. doi:10.1214/aoms/1177704481.
55b. Crooks G E (2010) The Amoroso Distribution. arXiv datbase ID:10053274: 1-6.
56. Lienhard J H, Meyer P L (1967) A physical basis for the generalized gamma distribution. Quart J Appl Math 25: 550-554.
57. Khodabin M, Ahmadabadi A (2010) Some properties of generalized gamma distribution. Math Sci 4: 9-28.
58. Suksaengrakcharoen S, Bodhisuwan W (2014) A new family of generalized gamma distribution and its application. J Math Stat 10: 211-220. doi:doi:10.3844/jmssp.2014.211.220.
59. Akaike H (1974) A new look at the statistical model identification. IEEE Trans Autom Control 19: 716-723. doi:10.1109/TAC. 1974.1100705.
60. Schwarz G (1978) Estimating the dimension of a model. Ann Stat 6: 461-464. doi:10.1214/aos/1176344136.
61. Geistlinger L, Csaba G, Kuffner R, Mulder N, Zimmer R (2011) From sets to graphs: towards a realistic enrichment analysis of transcriptomic systems. Bioinformatics 27: i366-i373. doi:10.1093/bioinformatics/btr228.
62. Geistlinger L (2015) EnrichmentBrowser: Seamless navigation through combined results of set-based and network-based enrichment analysis. R package version 2.1.0: 1-15.
63. Sanchez R, Mackenzie S "Information Thermodynamics of Cytosine DNA Methylation" PLoS One. 2016; 11(3): e0150427. Published online 2016 Mar. 10. doi: 10.1371/journal.pone.0150427.
64. Sanchez R, Mackenzie S "Genome-Wide Discriminatory Information Patterns of Cytosine DNA Methylation" Int J Mol Sci. 2016 June; 17(6): 938. Published online 2016 Jun. 17. doi: 10.3390/ijms17060938.
65. Lienhard J H, Meyer P L (1967) A physical basis for the generalized gamma distribution. Quart J Appl Math 25: 550-554.
66. Stacy E W (1962) A Generalization of the Gamma Distribution. Ann Math Stat 33: 1187-1192. doi:10.1214/aoms/1177704481.

What is claimed is:

1. A computer-implemented method of preparing a set of differentially informative methylated positions (DIMPs) or differentially informative methylated regions (DIMRs) from sample methylome data of an animal or plant having a phenotypic characteristic different from a wild-type of the same species of animal or plant, comprising:
providing a computer with the sample methylome data, and reference methylome data of the wild-type of the same species of animal or plant;
calculating with the computer an information-divergence between the methylation level of each cytosine position of the sample methylome data and the reference methylome data;
fitting the information-divergences to a generalized gamma distribution and selecting a threshold value from the fitting; and
selecting with the computer each cytosine position having an information-divergence above the threshold value to form a set of DIMPs, or selecting with the computer each region of cytosine positions having a sum of divergences above the threshold value to form a set of DIMRs.

2. The method of claim 1, wherein the information-divergence is a Hellinger divergence, $H_R^D$.

3. The method of claim 1, wherein the selecting fitting comprises:
calculating with the computer a non-linear fit of a first equation, with a non-linear regression analysis, of the empirical cumulative distribution function of the information-divergence $D_R$ versus $D_R$, to obtain an estimation of $\hat{F}(D_R^D \leq D_R^0 | \hat{\alpha}, \hat{\mu}, \hat{\lambda}, \hat{\psi})$, and values for shape parameters $\hat{\alpha}$, $\hat{\lambda}$, $\hat{\mu}$ and $\hat{\psi}$ through the equation $$F(D_R \mid \hat{\alpha}, \hat{\lambda}(l), \hat{\mu}, \hat{\psi}) = \begin{cases} \frac{1}{\Gamma(\hat{\psi})} \gamma\left(\hat{\psi}, \left(\frac{D_R - \hat{\mu}}{\hat{\lambda}(l)}\right)^{\hat{\alpha}}\right) & \hat{\psi} > 0 \\ 1 - \frac{1}{\Gamma(\hat{\psi})} \gamma\left(\hat{\psi}, \left(\frac{D_R - \hat{\mu}}{\hat{\lambda}(l)}\right)^{\hat{\alpha}}\right) & \hat{\psi} \leq 0 \end{cases};$$

wherein the first equation is substantially any member of the generalized gamma distribution family $\hat{F}(D_R \leq D_R^0 | \ldots)$ or includes the empirical cumulative function $$\hat{F}_n(D_R \le D_R^0) = \frac{1}{n}\sum_{k=1}^{n} 1_{D_R \le \hat{D}_R^0}$$

directly or through a non-linear fit to an empirical function and each $D_R^0$ is substituted with the information-divergence, when calculating the non-linear fit, 1 is genomic region length and y is the incomplete gamma function;

calculating with the computer $\alpha_0^k = 1 - \hat{F}(H_R^D \le H_R^{D_0} | \hat{\alpha}, \hat{\mu}, \hat{\lambda}, \hat{\psi})$, or $\alpha_0^k = 1 - \hat{F}(H_R^D \le H_R^{D_0} | \ldots)$ with a cumulative distribution function $\hat{F}(H_R^D \le H_R^{D_0} | \ldots)$ of any member of the generalized gamma distribution family or includes the empirical cumulative function $a_0^R = 1 - \hat{F}(H_R^D \le H_R^{D_0})(D_R^0 = H_R^{D_0})$ at each genomic region R or cytosine position k where R=k, of the methylome; and selecting the threshold value to result in the selecting with the computer a set of DIMRs or DIMPs at a level of significance $\alpha$ for the methylome data by only including those genomic regions or cytosine positions where $\alpha_0^R$ or $\alpha_0^k$ is less than $\alpha$ ($\alpha_0^R \le \alpha$ or $\alpha_0^k \le \alpha$), respectively, wherein $\alpha$ is at most 0.10.

4. The method of claim 3, wherein a is at most 0.07.

5. The method of claim 3, wherein a is at most 0.05.

6. The method of claim 5, wherein the sample methylome data are sample methylome data of a plant.

7. The method of claim 5, wherein the plant is selected from the group consisting of corn, wheat, rice, sorghum, millet, tomatoes, potatoes, soybeans, tobacco, cotton, canola, alfalfa, rapeseed, sugar beets and sugarcane.

8. The method of claim 5, wherein the sample methylome data a sample methylome data of a mammal.

9. The method of claim 5, wherein the mammal is a human.

10. The method of claim 9, wherein the human is a human with a pathological condition.

11. The method of claim 8, wherein the mammal is a mouse, rat, goat, sheep, cow, horse, dog, cat or camel.

12. The method of claim 11, wherein the mammal is a mammal with a pathological condition.

13. A method of preparing a collection of sets of DIMPs or DIMRs from a plurality of sample methylomes data sets each prepared from one of a plurality of animals or plants, each animal or plant being of the same species and each animal or plant having the same or similar phenotypic characteristic different from wild-type of the same species, comprising:

preparing a set of DIMPs or DIMRs for each sample methylome data set, using a single reference methylome data set, wherein each set of DIMPs or DIMRs is prepared by the method of claim 1.

14. The method of claim 13, wherein the sample methylome data sets are sample methylome data sets of plants.

15. A method of selecting positions and/or regions of differential methylation indicative of a phenotypic characteristic from a plurality of sample methylome data sets of different animals or plants of a single species, at least one having the phenotypic characteristic different from a wild-type of the same species, comprising:

providing a computer with the sample methylome data sets, a reference methylome data set of the wild-type of the same species, and a collection of DIMPs or DIMRs prepared by the method of claim 13; and selecting positions and/or regions of differential methylation indicative of the phenotypic characteristic.

16. The method of claim 15, wherein the selecting comprises visually comparing the DIMPs or DIMRs of each methylome data set with each other.

17. The method of claim 15, wherein the selecting comprises selecting regions of differential methylation and the regions are discriminatory informative genomic regions (DIGRs).

18. The method of claim 17, wherein the selecting comprises a computer-implemented method, comprising:

splitting a genome associated with the species into a plurality of N genomic regions;

a first step of calculating with the computer a Hellinger distance, $H_R^D$, for each genomic region of each sample methylome data set, wherein the Hellinger distance is the sum of Hellinger divergence of the DIMPs or DIMRs in each region from the reference methylome data, to produce a first vector in N-dimensional space composed of the Hellinger distances of each sample methylome data set;

a second step of calculating with the computer a classification of the first vectors for the characteristic with a de novo classifier algorithm;

a third step of calculating with the computer a reduced dimensionality of the space of the first vectors by performing feature extraction to obtain principal components using a factor analysis algorithm, to produce reduced dimensionality vectors;

a fourth step of repeating the second step of calculating using the reduced dimensionality vectors;

a fifth step of calculating with the computer to carry out an iteratively cross-validation of the reduced dimensionality vectors, with each step of the iteratively cross-validation being a plurality of ten-fold cross validations to obtain the prior classification used in the second calculating that produces a maximum classification accuracy of the reduced dimensionality vectors for the characteristic, wherein the maximum classification accuracy is at least 90%;

a sixth step of calculating with the computer to select features of the reduced dimensionality vectors based on the contributions of the original vectors to the principal components;

a seventh step of selecting with the computer a subset of the genomic regions with major contribution to the principal component analysis;

an eighth step of forming second vectors from the subset of the genomic regions selected in the seventh step;

a ninth step of repeating the third step through the eighth step until a minimal subset of genomic regions is found which is able to classify the plurality of sample methylome data sets with a maximum classification accuracy of the different animals or plants having a phenotypic characteristic, wherein the minimal subset of genomic regions is the set of DIGRs, and the classification accuracy of the DIGRs is not less than the classification accuracy of the genomic regions prepared in the splitting.

19. A method of preparing a set of plants harboring a phenotypic characteristic associated with differences in methylation of the genome, comprising:

preparing epigenetic variants of a wild-type plant;

breeding the plant, to prepare progeny plants;

selecting positions and/or regions of differential methylation indicative of the phenotypic characteristic by the method of claim 15; and preparing the set of plants by selecting those plants having the positions and/or regions of differential methylation indicative of the characteristic in their methylome.

20. The method of claim 5, wherein the information-divergence is a Hellinger divergence, $H_R^D$.

21. The method of claim 13, wherein the information-divergence is a Hellinger divergence, $H_R^D$.

22. The method of claim 19, wherein the information-divergence is a Hellinger divergence, $H_R^D$.

* * * * *

UNITED STATES PATENT AND TRADEMARK OFFICE
CERTIFICATE OF CORRECTION

Page 1 of 1

PATENT NO. : 10,913,986 B2
APPLICATION NO. : 15/422409
DATED : February 9, 2021
INVENTOR(S) : Sally A. Mackenzie et al.

It is certified that error appears in the above-identified patent and that said Letters Patent is hereby corrected as shown below:

In the Claims

Column 32, Claim 3, Line 48, please delete "selecting"
Column 33, Claim 3, Line 8, please delete "1" and insert --*l*--
Column 33, Claim 3, Line 9, please delete "y" and insert --γ--
Column 33, Claim 4, Line 23, please delete "a" and insert --α--
Column 33, Claim 5, Line 24, please delete "a" and insert --α--
Column 33, Claim 8, Line 32, please delete "a sample" and insert --are sample--

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*